United States Patent [19]

Himmelsbach et al.

[11] Patent Number: 5,612,335

[45] Date of Patent: Mar. 18, 1997

[54] CYCLIC COMPOUNDS AND PHARMACEUTICAL COMPOSITIONS CONTAINING THEM

[75] Inventors: F. Himmelsbach, Mittelbiberach; Helmut Pieper; Volkhard Austel, both of Biberach; Gunter Linz, Mittelbiberach; Brian Guth, Warthausen; Thomas Muller; Johannes Weisenberger, both of Biberach, all of Germany

[73] Assignee: Karl Thomae GmbH, Biberach an der Riss, Germany

[21] Appl. No.: 434,136

[22] Filed: May 2, 1995

Related U.S. Application Data

[62] Division of Ser. No. 200,125, Feb. 22, 1994, Pat. No. 5,519,036.

[30] Foreign Application Priority Data

Feb. 22, 1993 [DE] Germany .......................... 43 05 388.2
Sep. 22, 1993 [DE] Germany .......................... 43 32 168.2

[51] Int. Cl.⁶ .......................... C07D 223/16; A61K 31/55
[52] U.S. Cl. .......................... 514/221; 540/594
[58] Field of Search .......................... 540/594; 514/213, 514/221

[56] References Cited

U.S. PATENT DOCUMENTS

| | | | |
|---|---|---|---|
| 5,242,929 | 9/1993 | Varasi et al. | 514/305 |
| 5,401,750 | 3/1995 | Varasi et al. | 514/299 |

FOREIGN PATENT DOCUMENTS

| | | | |
|---|---|---|---|
| 0505778 | 3/1992 | European Pat. Off. | 514/305 |

*Primary Examiner*—Zinna Northington Davis
*Attorney, Agent, or Firm*—R. P. Raymond; M-E. M. Devlin; A. R. Stempel

[57] ABSTRACT

The invention relates to cyclic derivatives of general formula

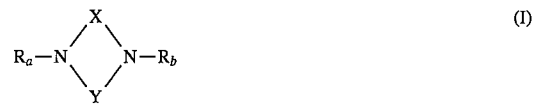

wherein $R_a$, $R_b$, X and Y are as defined in claim 1, the tautomers, the stereoisomers including the mixtures thereof and the salts thereof, particularly the physiologically acceptable salts thereof with organic or inorganic acids or bases, which have valuable pharmacological properties, preferably aggregation-inhibiting effects, pharmaceutical compositions containing the compounds and processes for preparing them.

6 Claims, No Drawings

CYCLIC COMPOUNDS AND PHARMACEUTICAL COMPOSITIONS CONTAINING THEM

This is a division of application Ser. No. 08/200,125, filed Feb. 22, 1994 now U.S. Pat. No. 5,519,036.

The invention relates to cyclic derivatives of general formula

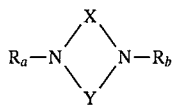
(I)

the tautomers, the stereoisomers including the mixtures thereof and the salts thereof, particularly the physiologically acceptable salts thereof with inorganic or organic acids or bases which have, inter alia, valuable pharmacological properties, preferably aggregation-inhibiting properties, to pharmaceutical compositions containing these compounds, to their use and to processes for preparing them.

In general formula I above:

X denotes a carbimino group optionally substituted at the nitrogen atom by an alkyl, aryl, heteroaryl or cyano group, or a carbonyl, thiocarbonyl, sulphonyl, 1-nitro-ethen-2,2-diyl or 1,1-dicyano-ethen-2,2-diyl-group;

Y denotes a straight chain $C_{2-4}$-alkylene or alkenylene group which is optionally substituted by $R_c$ or $R_d$ or by $R_c$ and $R_d$, and which may additionally be substituted by one or two alkyl groups and wherein additionally one or two methylene groups may each be replaced by a carbonyl group, or a 1,2-cycloalkylene group containing 5 to 7 carbon atoms optionally substituted by $R_c$ or $R_d$ or by $R_c$ and $R_d$, or a 1,2-cycloalkenylene group containing 5 to 7 carbon atoms optionally substituted by $R_c$ or $R_d$ or by $R_c$ and $R_d$, or a 1,2 arylene group, or a 1,2 phenylene group in which one or two methine groups are each replaced by a nitrogen atom or wherein one or two —CH=CH— groups are each replaced by a —CO—NH group or wherein one methine group is replaced by a nitrogen atom and one —CH=CH— group is replaced by a —CO—NH group, whilst the above-mentioned heterocyclic groups may additionally be substituted by one or two alkyl groups, or a —CO—NH—, —NH—CO—, —CH=N— or —N=CH— group optionally substituted by $R_c$ or $R_d$, a first of the groups $R_a$ to $R_d$ denotes an A-B group wherein A is a group of one of the formulae

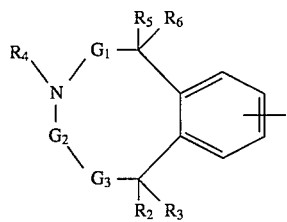

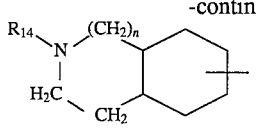

and

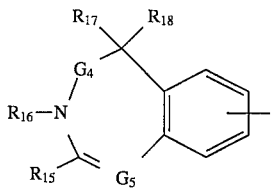

wherein the benzo moiety of the above-mentioned groups may be mono-substituted by $R_{25}$, or mono- or di-substituted by $R_{26}$, or mono-substituted by $R_{25}$ and additionally mono-substituted by $R_{26}$, wherein the substituents $R_{25}$ and $R_{26}$, which may be identical or different, are defined as follows, and additionally in the above-mentioned benzo moiety one to three methine groups may each be replaced by a nitrogen atom, or a —CH=CH— group may be replaced by a —CO—NR$_1$— group, or a methine group may be replaced by a nitrogen atom and a CH=CH— group by a —CO—NR$_1$ group, wherein $R_1$ denotes a hydrogen atom or an alkyl group, $G_1$ and $G_4$ each represent a bond or a methylene group which may be mono or disubstituted by an alkyl, aryl or a heteroaryl group, wherein the substituents may be identical or different, $G_2$ denotes a bond or a methylene group substituted by $R_7$ and $R_8$, $G_3$ denotes a bond or a methylene group substituted by $R_9$ and $R_{10}$, or, if $G_2$ does not denote a bond, $G_3$ may also denote a carbonyl group, $G_5$ denotes a nitrogen atom or a methine group optionally substituted by an alkyl, aryl or heteroaryl group, $R_2$ denotes a hydrogen atom or an alkyl, aryl or heteroaryl group or, if at least one of $G_2$ and $G_3$ does not denote a bond, $R_2$ may also denote a hydroxy or alkoxy group, $R_3$ denotes a hydrogen atom or an alkyl, aryl or heteroaryl group, or, if at least one of groups $G_2$ and $G_3$ does not denote a bond, $R_3$ together with $R_2$ may also denote an oxygen atom, $R_4$ and $R_{14}$ each denote a hydrogen atom, a cycloalkyl or cycloalkylalkyl group each having 3 to 7 carbon atoms in the cycloalkyl moiety, a $C_{1-8}$-alkyl group, a $C_{3-8}$-alkenyl group (which alkenyl group may not be connected to the nitrogen atom via the vinyl moiety), or a hydroxyalkyl, alkoxyalkyl, aminoalkyl, alkylaminoalkyl, dialkylaminoalkyl, cyanoalkyl, carboxyalkyl, alkoxycarbonylalkyl, aminocarbonylalkyl, N-alkylaminocarbonylalkyl, N,N-dialkylaminocarbonylalkyl, arylalkyl, heteroarylalkyl, alkoxycarbonyl, arylmethyloxycarbonyl, formyl, acetyl, trifluoroacetyl, allyloxycarbonyl, amidino or $R_{11}CO-O-(R_{12}CR_{13})-O-CO$ group, wherein $R_{11}$ denotes a $C_{1-8}$ alkyl group, a $C_{5-7}$ cycloalkyl group or an aryl or arylalkyl group, $R_{12}$ denotes a hydrogen atom, an alkyl group, a $C_{5-7}$ cycloalkyl group or an aryl group and $R_{13}$ denotes a hydrogen atom, or an alkyl group, or $R_4$ together with $R_3$ denotes a straight chain alkylene group having a 2 to 4 carbon atoms or, if $G_2$ does not represent a bond, $R_4$ may denote a methylene group, $R_5$ denotes a hydrogen atom, an alkyl, aryl or heteroaryl group or, if $G_1$ does not represent a bond, $R_5$ may also denote a hydroxy or alkoxy group or, if $G_1$ does represent a bond, $R_4$ together with $R_5$ may denote another bond and $R_6$ represents a hydrogen atom, an alkyl, aryl or heteroaryl group or, if $G_1$ represents a bond and $R_4$ together with $R_5$ represents another bond, $R_6$ may represent a chlorine atom or a hydroxy, methoxy, amino, alkylamino, or dialkylamino group, or, if $G_1$ does not denote a bond, $R_6$ together with $R_5$ may denote an oxygen atom, $R_7$ denotes a hydrogen atom or an alkyl, aryl or heteroaryl group, $R_8$ denotes a hydrogen atom or an alkyl, aryl or heteroaryl group or $R_8$ together with $R_4$ may denote a straight chain $C_{2-5}$-alkylene group, $R_9$ denotes a hydrogen atom or an alkyl, aryl or heteroaryl group or, if $G_2$ does not represent a bond, $R_9$ may also represent a hydroxy or alkoxy group, $R_{10}$ denotes a hydrogen atom or an alkyl, aryl or heteroaryl group or $R_{10}$ together with $R_4$ may denote a straight chain $C_{2-4}$-alkylene group, $R_{15}$ denotes a hydrogen or chlorine atom or an alkyl, aryl, heteroaryl, hydroxy, methoxy, amino, alkylamino or dialkylamino group, $R_{16}$ denotes a hydrogen atom, a cycloalkyl or cycloalkylalkyl group each having 3 to 7 carbon atoms in the cycloalkyl moiety, a $C_{1-8}$-alkyl group, a $C_{3-8}$-alkenyl group (which alkenyl group may not be connected to the nitrogen atom via the vinyl group), or a hydroxyalkyl, alkoxyalkyl, aminoalkyl, alkylaminoalkyl, dialkylaminoalkyl, cyanoalkyl, carboxyalkyl, alkoxycarbonylalkyl, aminocarbonylalkyl, N-alkylaminocarbonylalkyl, N,N-dialkylaminocarbonylalkyl or aralkyl group, $R_{17}$ denotes a hydrogen atom or an alkyl group or, if $G_4$ denotes a bond, $R_{16}$ together with $R_{17}$ may denote another bond, $R_{18}$ denotes a hydrogen atom or an alkyl group or, if $G_4$ represents a bond and $R_{16}$ and $R_{17}$ together represent another bond, $R_{18}$ may denote a fluorine, chlorine or bromine atom or a hydroxy, methoxy, amino, alkylamino or dialkylamino group and n represents the number 1 or 2, and B denotes a bond, a $C_{1-6}$-alkylene, $C_{2-6}$-alkenylene, or arylene group, or a pyridinylene, pyrimidinylene, pyrazinylene, or pyridazinylene group, wherein one or two —CH=N— groups may each be replaced by a —CO—NH— group and one of the nitrogen atoms instead of being bound to a hydrogen atom may be bound to the group A, whilst the above-mentioned heterocyclic groups may additionally be substituted by one or two alkyl groups, or B denotes a $C_{4-7}$-cycloalkylene group optionally substituted by one or two alkyl groups, or a $C_{5-7}$-cycloalkylene group which is optionally substituted by one or two alkyl groups, and in which a >CH unit is replaced by a nitrogen atom, whilst additionally in the above-mentioned 5 to 7 membered rings a methylene group adjacent to a nitrogen atom may be replaced by a carbonyl group; a second of the groups $R_a$ to $R_d$ denotes a group of formula

F—E—D— wherein D denotes a $C_{1-6}$-alkylene group wherein a methylene group may be replaced by an oxygen or sulphur atom or by a sulphinyl, sulphonyl or $NR_{19}$ group, or wherein an ethylene group may be replaced by a —CO—$NR_{20}$— or —$NR_{20}$—CO— group (wherein $R_{19}$ denotes a hydrogen atom or an alkyl, alkylcarbonyl, alkylsulphonyl, arylcarbonyl or arylsulphonyl group and $R_{20}$ denotes a hydrogen atom or an alkyl group), or D denotes a $C_{2-6}$-alkenylene, or an arylene group, or a pyridinylene, pyrimidinylene, pyrazinylene or pyridazinylene group wherein one or two —CH=N— groups may each be replaced by a —CO—NH— group and one of the nitrogen atoms, instead of being bound to a hydrogen atom, may be bound to the group E, provided that this does not itself represent a bond or does not adjoin the group D with a heteroatom or a carbonyl group, whilst the above-mentioned heterocyclic groups may additionally be substituted by one or two alkyl groups, or D denotes an indanylene, naphthylene, 1,2,3,4-tetrahydronaphthylene or benzosuberanylene group in which one of the rings is bound to the group E and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group, or a $C_{4-7}$-cycloalkylene group optionally substituted by one or two alkyl groups, or a $C_{5-7}$-cycloalkylene group which is optionally substituted by one or two alkyl groups and in which a >CH unit is replaced by a nitrogen atom, whilst moreover in the above-mentioned 5 to 7 membered rings a methylene group adjacent to a nitrogen atom may be replaced by a carbonyl group, or a piperazinylene group which is optionally substituted by one or two alkyl groups and in which a methylene group adjacent to a nitrogen atom may be replaced by a carbonyl group, or, if E represents a cyclic imino group, D may also denote an alkylenecarbonyl group having a total of 2 to 6 carbon atoms, wherein the carbonyl group is bound to the nitrogen atom of the cyclic imino group of group E, or, if E does not represent a bond, D may represent a bond, E denotes a bond, or a $C_{1-6}$-alkylene group which may be substituted by 1 or 2 $C_{1-8}$-alkyl groups, by a $C_{2-4}$-alkenyl or $C_{2-4}$-alkynyl group, by a hydroxy, amino, aryl or heteroaryl group, by a $C_{1-8}$-alkoxy or $C_{1-8}$-alkylamino group, by a dialkylamino group having a total of 2 to 10 carbon atoms, or by an $HNR_{21}$ or N-alkyl-$NR_{21}$ group, wherein $R_{21}$ denotes an alkylcarbonyl or alkylsulphonyl group each having 1 to 8 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, or an arylalkylcarbonyl, arylalkylsulphonyl, arylalkoxycarbonyl, arylcarbonyl or arylsulphonyl group, or a $C_{2-6}$ alkenylene group, or an arylene group, or a pyridinylene, pyrimidinylene, pyrazinylene or pyridazinylene group optionally substituted by one or two alkyl groups, or a $C_{5-7}$-cycloalkylene group which is optionally substituted by one or two alkyl groups and in which a >CH unit is replaced by a nitrogen atom linked to a carbon atom of the group D, or a $C_{4-7}$-cycloalkylene group optionally substituted by one or two $C_{1-8}$-alkyl groups, by a $C_{2-4}$-alkenyl or $C_{2-}$-alkynyl group, by a hydroxy, amino, aryl or heteroaryl group, by a $C_{1-8}$-alkoxy or $C_{1-8}$-alkylamino group, by a dialkylamino group having a total of 2 to 10 carbon atoms, or by an $HNR_{21}$ or N-alkyl-$NR_{21}$, (wherein $R_{21}$ is as hereinbefore defined), or, if D does not denote a bond, an alkylene group linked to group D via a group W, wherein W denotes an oxygen or sulphur atom or a sulphinyl, sulphonyl, $NR_{19}$, $NR_{20}$—CO—, or —CO—$NR_{20}$— group, wherein $R_{19}$ and $R_{20}$ are as hereinbefore defined and the alkylene group may additionally be substituted by one or two $C_{1-8}$-alkyl groups, by a $C_{2-4}$-alkenyl or $C_{2-4}$-alkynyl group, by a hydroxy, amino, aryl or heteroaryl group, by a $C_{1-8}$alkoxy or $C_{1-8}$-alkylamino group, by a dialkylamino group containing a total of 2 to 10 carbon atoms, by an $HNR_{21}$ or N-alkyl-$NR_{21}$- group, wherein the heteroatom of the additional substituent is separated from a heteroatom of the group W by at least two carbon atoms and $R_{21}$ is as hereinbefore defined, and F denotes a carbonyl group substituted by a hydroxy group, by a $C_{1-8}$-alkoxy group, by an arylalkoxy group or by an $R_{22}O$ group, wherein $R_{22}$ denotes a $C_{4-8}$-cycloalkyl group or a cycloalkylalkyl group having 3 to 8 carbon atoms in the cycloalkyl moiety, wherein the cycloalkyl group may be substituted by an alkyl, alkoxy or dialkylamino group, by an alkyl group and by 1 to 3 methyl groups, and wherein additionally a methylene group in a 4 to 8 membered cycloalkyl ring may be replaced by an oxygen atom or by an alkylimino group, or $R_{22}$ denotes a $C_{9-12}$-benzocycloalkyl group or an aryl group, or F denotes a sulpho, phosphono, O-alkylphosphono, O,O'-dialkylphosphono, tetrazol-5-yl or $R_{23}CO$—O—$CHR_{24}$—O—CO group, wherein $R_{23}$ denotes a $C_{1-8}$-alkyl or $C_{1-8}$-alkoxy group, a cycloalkyl or cycloalkyloxy group each having 5 to 7 atoms in the cycloalkyl moiety, or an aryl, aryloxy, arylalkyl or arylalkoxy group and $R_{24}$ denotes a hydrogen atom or an alkyl group, and the shortest distance between the group F and the nitrogen atom of group A-B which is furthest from the group F is at least 11 bonds;

a third of the groups $R_a$ to $R_d$ denotes a hydrogen atom, an alkyl, perfluoroalkyl, alkoxy, alkylsulphenyl, alkylsulphinyl, alkylsulphonyl, amino, alkylamino, dialkylamino, aryl, heteroaryl or arylalkyl group; and the fourth of the groups $R_a$ to $R_d$ denotes a hydrogen atom or an alkyl or aryl group;

whilst unless otherwise specified each of the aryl moieties mentioned in the definition of the above groups is a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different and $R_{25}$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl or dialkylaminosulphonyl group, and $R_{26}$ denotes an alkyl, hydroxy or alkoxy group or a fluorine, chlorine, bromine or iodine atom, and if two $R_{26}$ groups are bound to adjacent carbon atoms they may also represent a $C_{3-6}$-alkylene group, a 1,3 butadien-1,4-diylene group or a methylenedioxy group, and each of the arylene moieties mentioned in the definition of the above-mentioned groups is a phenylene group which may be monosubstituted by $R_{25}$, mono or disubstituted by $R_{26}$, or monosubstituted by $R_{25}$ and additionally monosubstituted by $R_{26}$, wherein the substituents may be identical or different and are defined as hereinbefore, and each of the heteroaryl moieties mentioned in the definition of the above groups is a 5 membered heteoaromatic ring which contains an oxygen, sulphur or nitrogen atom, or a nitrogen atom and an oxygen, sulphur or nitrogen atom, or two nitrogen atoms and an oxygen, sulphur or nitrogen atom, or is a 6 membered heteroaromatic ring which contains 1, 2 or 3 nitrogen atoms and wherein additionally one or two —CH=N— groups may each be replaced by a —CO—$NR_{20}$— group (wherein $R_{20}$ is defined as hereinbefore), and additionally the above-mentioned heteroaromatic rings may be substituted by one or two alkyl groups or, on the carbon skeleton, by a fluorine, chlorine, bromine or iodine atom or by a hydroxy or alkoxy group, and unless otherwise specified, the above-mentioned alkyl, alkylene and alkoxy moieties may each contain 1 to 4 carbon atoms, and each carbon atom in the above mentioned alkylene and cycloalkylene moieties is linked to one heteroatom at most and the tautomers, stereoisomers and salts thereof.

Preferred compounds of the above general formula I, however, are those wherein:

X denotes a carbimino group optionally substituted at the nitrogen atom by an alkyl or cyano group, or X denotes a carbonyl, thiocarbonyl or sulphonyl group;

Y represents a straight chain $C_{2-3}$-alkylene group which is optionally substituted by $R_c$ or $R_d$, or by $R_c$ and $R_d$, and which may additionally be substituted by 1 or 2 alkyl groups and wherein additionally a methylene group may be replaced by a carbonyl group, or a straight chain $C_{2-3}$-alkenylene group which is optionally substituted by $R_c$ or $R_d$, or by $R_c$ and $R_d$, and in which additionally any methylene group present may be replaced by a carbonyl group, or a 1,2-cycloalkylene group with 5 to 7 carbon atoms optionally substituted by $R_c$ or $R_d$, or by $R_c$ and $R_d$, or a 1,2-cycloalkenylene group with 5 to 7 carbon atoms, or a 1,2-arylene group, or a 1,2-phenylene group, wherein 1 or 2 methine groups are each replaced by a nitrogen atom, wherein the above-mentioned heterocyclic groups may additionally be substituted by 1 or 2 alkyl groups, or a —CO—NH—, —NH—CO—, —CH=N— or —N=CH— group optionally substituted by $R_c$ or $R_d$;

a first of the groups $R_a$ to $R_d$ denotes an A-B group wherein

A is a group of one of the formulae

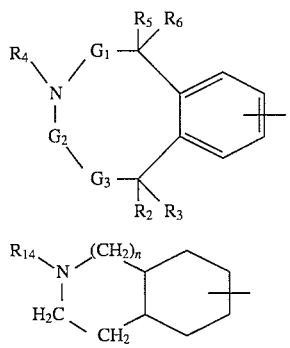

and

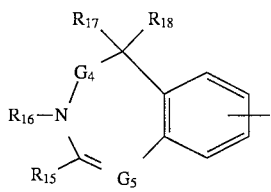

wherein the benzo moiety of the above-mentioned groups may be monosubstituted by $R_{25}$, or mono- or di-substituted by $R_{26}$, or mono-substituted by $R_{26}$, wherein the substituents $R_{25}$ and $R_{26}$, which may be identical or different, are defined as follows, and additionally in the above-mentioned benzo moiety, one to three methine groups may each be replaced a nitrogen atom or a —CH=CH group may be replaced by a —CO—$NR_1$ group, or a methine group may be replaced by a nitrogen atom and a —CH=CH group by a —CO—$NR_1$ group, wherein $R_1$ denotes a hydrogen atom or an alkyl group, $G_1$ and $G_4$ each represent a bond or a methylene group which may be mono or disubstituted by an alkyl or aryl group, wherein the substituents may be identical or different, $G_2$ denotes a bond or a methylene group substituted by $R_7$ and $R_8$, $G_3$ denotes a bond or a methylene group substituted by $R_9$ and $R_{10}$, $G_5$ denotes a nitrogen atom or a methine group optionally substituted by an alkyl or aryl group, $R_2$ denotes a hydrogen atom or an alkyl, aryl or a heteroaryl group or, if at least one of $G_2$ and $G_3$ does not represent a bond, $R_2$ may also denote a hydroxy or alkoxy group, $R_3$ denotes a hydrogen atom or an alkyl or aryl group, $R_4$ and $R_{14}$ each denote a hydrogen atom, a cycloalkyl or cycloalkylalkyl group each having 3 to 7 carbon atoms in the cycloalkyl moiety, a $C_{1-6}$-alkyl group, a $C_{3-6}$-alkenyl group (which alkenyl group may not be linked to the nitrogen atom via the vinyl moiety), a hydroxyalkyl, alkoxyalkyl, carboxyalkyl, alkoxycarbonylalkyl, aminocarbonylalkyl, N-alkylaminocarbonylalkyl, N,N-dialkylaminocarbonylalkyl, arylalkyl, alkoxycarbonyl, arylmethyloxycarbonyl, formyl, acetyl, trifluoroacetyl, allyloxycarbonyl, amidino or $R_{11}CO$—O—($R_{12}CR_{13}$)—O—CO— group, wherein $R_{11}$ denotes a $C_{1-8}$-alkyl group, a $C_{5-7}$-cycloalkyl group or an aryl or arylalkyl group, $R_{12}$ denotes a hydrogen atom, an alkyl group, a $C_{5-7}$-cycloalkyl group or an aryl group, and $R_{13}$ denotes a hydrogen atom, or $R_4$ together with $R_3$ may denote a straight chain $C_{2-4}$-alkylene group or, if $G_2$ does not represent a bond, a methylene group, $R_5$ denotes a hydrogen atom, an alkyl or aryl group or, if $G_1$ does not represent a bond, a hydroxy or alkoxy group or, if $G_1$ does represent a bond, $R_4$ together with $R_5$ may represent another bond, and $R_6$ denotes a hydrogen atom or an alkyl or aryl group or, if $G_1$ denotes a bond and $R_4$ together with $R_5$ denotes another bond, $R_6$ may denote a chlorine atom or a hydroxy, methoxy, amino, alkylamino or dialkylamino group, $R_7$ denotes a hydrogen atom or an alkyl or aryl group, $R_8$ denotes a hydrogen atom or an alkyl or aryl group or $R_8$ together with $R_4$ may denote a straight chain $C_{2-5}$-alkylene group, $R_9$ denotes a hydrogen atom or an alkyl or aryl group or, if $G_2$ does not represent a bond, $R_9$ may denote a hydroxy or alkoxy group, $R_{10}$ denotes a hydrogen atom or an alkyl or aryl group, or $R_{10}$ together with $R_4$ may denote a straight chain $C_{2-4}$-alkylene group, $R_{15}$ denotes a hydrogen or chlorine atom or an alkyl, aryl, hydroxy, methoxy, amino, alkylamino or dialkylamino group, $R_{16}$ denotes a hydrogen atom, a cycloalkyl or cycloalkylalkyl group each having 3 to 7 carbon atoms in the cycloalkyl moiety, a $C_{1-6}$-alkyl group, a $C_{3-6}$-alkenyl group (which alkenyl group may not be connected to the nitrogen atom via the vinyl group), or a hydroxyalkyl, alkoxyalkyl, carboxyalkyl, alkoxycarbonylalkyl, aminocarbonylalkyl, N-alkylaminocarbonylalkyl, N,N-dialkylaminocarbonylalkyl or arylalkyl group, $R_{17}$ represents a hydrogen atom or an alkyl group or, if $G_4$ denotes a bond, $R_{16}$ together with $R_{17}$ may denote another bond, $R_{18}$ denotes a hydrogen atom or an alkyl group or, if $G_4$ represents a bond and $R_{16}$ and $R_{17}$ together represent another bond, $R_{18}$ may denote a fluorine, chlorine or bromine atom or a hydroxy, methoxy, amino, alkylamino or dialkylamino group, and n represents the number 1 or 2, and B denotes a bond or an alkylene or arylene group, or a pyridinylene, pyrimidinylene, pyrazinylene, or pyridazinylene group, wherein one or two —CH=N— groups may each be replaced by a —CO—NH— group, whilst the above-mentioned heterocyclic groups may additionally be substituted by one or two alkyl groups, or a $C_{4-7}$-cycloalkylene group optionally substituted by one or two alkyl groups, or a $C_{5-7}$-cycloalkylene group which is optionally substituted by one or two alkyl groups, and in which a >CH unit is replaced by a nitrogen atom, whilst additionally, in the above-mentioned 5 to 7 membered rings, a methylene group adjacent to a nitrogen atom may be replaced by a carbonyl group;

a second of the groups $R_a$ to $R_d$ denotes a group of the formula

F—E—D— wherein

D denotes a $C_{1-6}$-alkylene group wherein a methylene group may be replaced by an oxygen or sulphur atom or by a sulphinyl, sulphonyl or $NR_{19}$ group, or wherein an ethylene group may be replaced by a —CO—$NR_{20}$ or —$NR_{20}$—CO group, (wherein $R_{19}$ denotes a hydrogen atom or an alkyl, alkylcarbonyl, alkylsulphonyl, arylcarbonyl or arylsulphonyl group, and $R_{20}$ denotes a hydrogen atom or an alkyl group), or a $C_{2-6}$ alkenylene or arylene group, or a pyridinylene, pyrimidinylene, pyrazinylene or pyridazinylene group wherein one or two —CH=N— groups may each be replaced by a —CO—NH— group, whilst the above-mentioned heterocyclic groups may additionally be substituted by one or two alkyl groups, or an indanylene, naphthylene, 1,2,3,4-tetrahydronaphthylene or benzosuberanylene group in which one of the rings is bound to the group E and the other ring is bound to the cyclic group of general formula I, whilst the saturated rings may each be substituted by one or two alkyl groups and the aromatic rings may each be substituted by a fluorine, chlorine, bromine or iodine atom or by an alkyl, trifluoromethyl, hydroxy, alkoxy, alkylsulphenyl, alkylsulphinyl, alkylsulphonyl or cyano group, or a $C_{4-7}$-cycloalkylene group optionally substituted by one or two alkyl groups, or a $C_{5-7}$-cycloalkylene group which is optionally substituted by one or two alkyl groups and in which a >CH unit is replaced by a nitrogen atom, whilst moreover in the above-mentioned 5 to 7 membered rings a methylene group adjacent to a nitrogen atom may be replaced by a carbonyl group, or a piperazinylene group which is optionally substituted by one or two alkyl groups, and in which a methylene group adjacent to a nitrogen atom may be replaced by a carbonyl group, or, if E represents a cyclic imino group, D may also denote an alkylenecarbonyl group having a total of 2 to 6 carbon atoms, the carbonyl group being bound to the nitrogen atom of the cyclic imino group of group E, or, if E does not represent a bond, D may also represent a bond, E denotes a bond, or a $C_{1-6}$-alkylene group which may be substituted by 1 or 2 $C_{1-6}$-alkyl groups, by a hydroxy, amino or aryl group, by an alkoxy or alkylamino group each having 1 to 6 carbon atoms, by a dialkylamino group having a total of 2 to 8 carbon atoms or by an $HNR_{21}$ or N-alkyl-$NR_{21}$— group (wherein $R_{21}$ denotes an alkylcarbonyl or alkylsulphonyl group each having 1 to 6 carbon atoms in the alkyl moiety, a alkyloxycarbonyl group having a total of 2 to 5 carbon atoms, a cycloalkylcarbonyl or cycloalkylsulphonyl group each having 5 to 7 carbon atoms in the cycloalkyl moiety, an arylalkylcarbonyl, arylalkylsulphonyl, arylalkoxycarbonyl, arylcarbonyl or arylsulphonyl group), or a $C_{2-6}$-alkenylene group, or an arylene group, or a pyridinylene, pyrimidinylene, pyrazinylene or pyridazinylene group optionally substituted by one or two alkyl groups.

or a $C_{5-7}$-cycloalkylene group which is optionally substituted by one or two alkyl groups and in which a >CH unit is replaced by a nitrogen atom linked to a carbon atom of the group D, or a cycloalkylene group having 4 to 7 carbon atoms in the cycloalkylene moiety, optionally substituted by one or two $C_{1-6}$-alkyl groups, by a hydroxy, amino or aryl group, by a $C_{1-6}$-alkoxy or $C_{1-6}$-alkylamino group, by a dialkylamino group having a total of 2 to 8 carbon atoms or by an $HNR_{21}$ or N-alkyl-$NR_{21}$— group (wherein $R_{21}$ is hereinbefore defined), or, if D does not represent a bond, E may denote an alkylene group linked to group D via a group W, wherein W represents an oxygen or sulphur atom, a sulphinyl, sulphonyl, —$NR_{19}$—, —$NR_{20}$—CO— or —CO—$NR_{20}$— group, wherein $R_{19}$ and $R_{20}$ are as hereinbefore defined and the alkylene group may additionally be substituted by one or two $C_{1-6}$-alkyl groups, by a hydroxy, amino or aryl group, by an alkoxy or alkylamino group each having 1 to 6 carbon atoms, by a dialkylamino group having a total of 2 to 8 carbon atoms or by an $HNR_2$ or N-alkyl-$NR_{21}$— group, wherein the heteroatom of the additional substituent is separated from a heteroatom of group W by at least two carbon atoms and $R_{21}$ is as herein before defined, and F denotes a carbonyl group substituted by a hydroxy group, by a $C_{1-6}$-alkoxy group, by an arylalkoxy group or by an $R_{22}O$ group (wherein $R_{22}$ denotes a $C_{4-7}$-cycloalkyl group or a cycloalkylalkyl group having 3 to 7 carbon atoms in the cycloalkyl moiety, wherein the cycloalkyl group may be substituted by an alkyl, alkoxy or dialkylamino group or by an alkyl group and by 1 to 3 methyl groups and additionally a methylene group in a 5 to 7 membered cycloalkyl ring may be replaced by an oxygen atom or by an alkylimino group, or $R_{22}$ denotes a $C_{9-11}$-benzocycloalkyl group), or a phosphono, O-alkylphosphono, O,O'-dialkylphosphono, tetrazol-5-yl or $R_{23}$CO—O—$CHR_{24}$—O—CO group, wherein $R_{23}$ denotes an alkyl or alkoxy group each having 1 to 8 carbon atoms, a cycloalkyl or cycloalkyloxy group each having 5 to 7 atoms in the cycloalkyl moiety or an aryl, aryloxy, arylalkyl or arylalkoxy group and $R_{24}$ denotes a hydrogen atom or an alkyl group, and the shortest distance between the group F and the nitrogen atom of group A-B which is furthest from the group F is at least 11 bonds;

a third of the groups $R_a$ to $R_d$ denotes a hydrogen atom, an alkoxy group (which alkoxy group cannot be bound to a nitrogen atom) an alkyl, trifluoromethyl, aryl, arylalkyl, thienyl, thiazolyl, pyridyl, pyrimidyl, pyrazinyl or pyridazinyl group; and a fourth of the groups $R_a$ to $R_d$ denotes a hydrogen atom or an alkyl group;

whilst unless otherwise specified each of the aryl moieties mentioned in the definition of the above groups is a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different, and $R_{25}$ denotes a cyano, aminocarbonyl, alkylaminocarbonyl, dialkylaminocarbonyl, alkylcarbonyl, alkylsulphenyl, alkylsulphinyl, alkylsulphonyl or trifluoromethyl group and $R_{26}$ denotes an alkyl, hydroxy or alkoxy group or a fluorine, chlorine, or bromine atom, whilst if two $R_{26}$ groups are bound to adjacent carbon atoms they may also represent a $C_{3-6}$-alkylene group, a 1,3 butadien-1,4-diylene group or a methylenedioxy group, and each of the arylene moieties mentioned in the definition of the above-mentioned groups is a phenylene group which may be monosubstituted by $R_{25}$, or mono or disubstituted by $R_{26}$, or monosubstituted by $R_{25}$ and additionally monosubstituted by $R_{26}$, wherein the substituents may be identical or different and are defined as hereinbefore;

and unless otherwise specified, the above-mentioned alkyl, alkylene or alkoxy moieties may each contain 1 to 4 carbon atoms, and each carbon atom in the above mentioned alkylene and cycloalkylene moieties is linked to one heteroatom at most;

and the tautomers, stereoisomers and salts thereof.

Particularly preferred are those compounds of general formula I wherein,

X denotes a carbimino group substituted at the nitrogen atom by a cyano group, or X denotes a carbonyl or sulphonyl group, Y denotes a $CH_2CH_2$—, $CH_2CH_2CH_2$—, —CH=CH, —$CH_2CO$— or —$COCH_2$— group optionally substituted by $R_c$, or by $R_c$ and $R_d$, or a —CO—NH—, —NH—CO—, CH=N—, or —N=CH group optionally substituted by $R_c$ or $R_d$;

a first of the groups $R_a$ to $R_d$ denote an A-B group wherein A is a group of one of the formulae

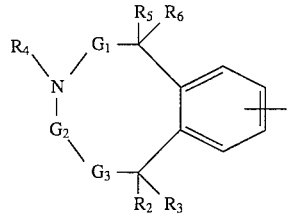

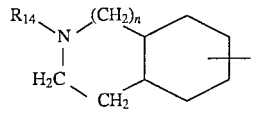

and

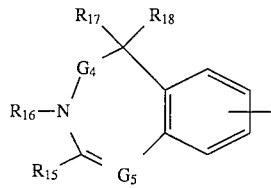

wherein the benzo moiety of the above-mentioned groups may be substituted by a fluorine, chlorine or bromine atom or by an alkyl, cyano, trifluoromethyl, hydroxy, alkoxy group, or 1 to 3 methine groups may each be replaced by a nitrogen atom, $G_1$ denotes a bond or a methylene group which may be mono or disubstituted by an alkyl group, whilst the substituents may be identical or different, $G_2$ denotes a bond or a methylene group substituted by $R_7$ and $R_8$, $G_3$ denotes a methylene group substituted by $R_9$ and $R_{10}$, $G_4$ denotes a bond, $G_5$ denotes a nitrogen atom or a methine group optionally substituted by an alkyl group, $R_2$ denotes a hydrogen atom or an alkyl group, $R_3$ denotes a hydrogen atom or an alkyl group, $R_4$ denotes a hydrogen atom, a cycloalkyl or cycloalkylalkyl group each having 3 to 7 carbon atoms in the cycloalkyl moiety, a $C_{1-6}$-alkyl group, a $C_{3-6}$-alkenyl group (which alkenyl group may not be linked to the nitrogen atom via the vinyl group), or a hydroxyalkyl, alkoxyalkyl, carboxyalkyl, alkoxycarbonylalkyl, aminocarbonylalkyl, N-alkylaminocarbonylalkyl, N,N-dialkylaminocarbonylalkyl, arylalkyl, alkoxycarbonyl, arylmethyloxycarbonyl, formyl, acetyl, trifluoroacetyl or $R_{11}CO$—O—$(R_{12}CR_{13})$—O—CO— group, (wherein $R_{11}$ denotes an alkyl group, $R_{12}$ denotes a hydrogen atom or an alkyl group, and $R_{13}$ denotes a hydrogen atom), or $R_4$ together with $R_3$ may denote a straight chain $C_{2-4}$-alkylene group, $R_5$ denotes a hydrogen atom or an alkyl group or, if $G_1$ denotes a bond, $R_4$ together with $R_5$ may denote another bond, $R_6$ denotes a hydrogen atom or an alkyl group or, if $G_1$ denotes a bond and $R_4$ together with $R_5$ denotes another bond, $R_6$ may denote an amino group, $R_7$ denotes a hydrogen atom or an alkyl group, $R_8$ denotes a hydrogen atom or an alkyl group, or $R_8$ together with $R_4$ may denote a straight chain $C_{3-4}$-alkylene group, $R_9$ denotes a hydrogen atom or an alkyl group, $R_{10}$ denotes a hydrogen atom or an alkyl group or $R_{10}$ together with $R_4$ may denote a straight chain $C_{3-4}$-alkylene group, $R_{14}$ denotes a hydrogen atom or an alkyl group, $R_{15}$ denotes a hydrogen atom or an alkyl group, $R_{16}$ denotes a hydrogen atom or an alkyl group, $R_{17}$ denotes a hydrogen atom or an alkyl group or together with $R_{17}$ may denote another bond, $R_{18}$ denotes hydrogen atom or an alkyl group or, if $R_{16}$ and $R_{17}$ together denote another bond, $R_{18}$ may denote a chlorine atom or an amino group, n represents the number 1 or 2, and B denotes a bond, or an alkylene group, or an arylene group, or a pyridinylene, pyrimidinylene, pyrazinylene, or pyridazinylene group, optionally substituted by 1 or 2 alkyl groups, or a cyclohexylene group optionally substituted by 1 or 2 alkyl groups, or a piperidinylene group which is optionally substituted by 1 or 2 alkyl groups, and in which a methylene group adjacent to a nitrogen atom may be replaced by a carbonyl group;

a second of the groups $R_a$ to $R_d$ denotes a group of formula

F—E—D— wherein

D denotes an alkylene group, or an arylene group, or a pyridinylene, pyrimidinylene, pyrazinylene or pyridazinylene group optionally substituted by 1 or 2 alkyl groups, or an indanylene, naphthylene, 1,2,3,4-tetrahydronaphthylene or benzosuberanylene group, wherein one of the rings is bound to the group E and the other ring to the cyclic group of general formula I, or a $C_{4-7}$-cycloalkylene group optionally substituted by 1 or 2 alkyl groups, or a $C_{5-7}$-cycloalkylene group which is optionally substituted by 1 or 2 alkyl group and in which a >CH unit is replaced by a nitrogen atom, whilst additionally in the above-mentioned 5 to 7 membered rings a methylene group adjacent to a nitrogen atom may be replaced by a carbonyl group, or, if E denotes a cyclic imino group, D may denote an alkylenecarbonyl group, wherein the carbonyl group is bound to the nitrogen atom of the cyclic imino group of group E, or if E does not represent a bond, D may also denote a bond, E denotes a bond, or an alkylene group which may be substituted by a $C_{1-6}$-alkyl group or by an amino, aryl, alkylamino, dialkylamino, $HNR_{21}$ or N-alkyl-$NR_{21}$-group (wherein $R_{21}$ denotes an alkylcarbonyl or alkylsulphonyl group each having 1 to 6 carbon atoms in the alkyl moiety, an alkyloxycarbonyl group having a total of 2 to 5 carbon atoms, a cycloalkylcarbonyl or cycloalkylsulphonyl group each having 5 to 7 carbon atoms in the cycloalkyl moiety, or an arylalkylcarbonyl, arylalkylsulphonyl, arylalkoxycarbonyl, arylcarbonyl or arylsulphonyl group), or a $C_{2-4}$-alkenylene group, or an arylene group, or a pyridinylene, pyrimidinylene, pyrazinylene or pyridazinylene group optionally substituted by one or two alkyl groups, or a $C_{5-7}$-cycloalkylene group which is optionally substituted by one or two alkyl groups and in which a >CH unit is replaced by a nitrogen atom linked to a carbon atom of the group D, or a $C_{4-7}$-cycloalkylene group optionally substituted by one or two alkyl groups, or, if D does not represent a bond, E may also denote an alkylene group linked to a group D via a group W, wherein W denotes an oxygen or sulphur atom or a sulphinyl, sulphonyl, —$NR_{20}$—CO— or —CO—$NR_{20}$— group, wherein $R_{20}$ denotes a hydrogen atom or an alkyl group and the alkylene group may additionally be substituted by a $C_{1-6}$-alkyl group, or by an amino, aryl, alkylamino, dialkylamino, $HNR_{21}$ or N-alkyl-$NR_{21}$-group, wherein the heteroatom of the additional substituent is separated from a heteroatom of group W by at least two carbon atoms and $R_{21}$ is as hereinbefore defined, and F denotes a carbonyl group substituted by a hydroxy, alkoxy, arylalkoxy or $R_{22}O$ group (wherein $R_{22}$ denotes a $C_{5-7}$-cycloalkyl group or a cycloalkylalkyl group having 5 to 7 carbon atoms in the cycloalkyl moiety), or an $R_{23}CO$—O—$CHR_{24}$—O—CO—, phosphono or O-alkylphosphono group, wherein $R_{23}$ denotes an alkyl, alkoxy, cycloalkyl or cycloalkyloxy group each having 5 to 7 carbon atoms in the cycloalkyl moiety and $R_{24}$ denotes a hydrogen atom or an alkyl group, and the shortest distance between the group F and the nitrogen atom of group A-B which is furthest from the group F is at least 11 bonds;

a third of the groups $R_a$ to $R_d$ denotes a hydrogen atom, an alkoxy group (which alkoxy group may not be bound to a nitrogen atom), or an alkyl, trifluoromethyl or aryl group; and the fourth of the groups $R_a$ to $R_d$ denotes a hydrogen atom or an alkyl group, whilst unless otherwise specified each of the aryl moieties mentioned in the definition of the above groups is a phenyl group which may be monosubstituted by $R_{25}$, mono, di or trisubstituted by $R_{26}$, or monosubstituted by $R_{25}$ and additionally mono or disubstituted by $R_{26}$, wherein the substituents may be identical or different and $R_{25}$ denotes a cyano, aminocarbonyl, alkylaminocarbonyl, dialkylaminocarbonyl, alkylcarbonyl, alkylsulphenyl, alkylsulphinyl, alkylsulphonyl or trifluoromethyl group and $R_{26}$ denotes an alkyl, hydroxy or alkoxy group or a fluorine, chlorine or bromine atom, whilst two groups $R_{26}$, if they are bound to adjacent carbon atoms, may also represent a straight chain $C_{3-4}$-alkylene group, a 1,3-butadien-1,4-diylene group or a methylenedioxy group, and each of the arylene moieties mentioned in the definition of the above-mentioned groups is a phenylene group which may be monosubstituted by $R_{25}$, mono or disubstituted by $R_{26}$, or monosubstituted by $R_{25}$ and additionally monosubstituted by $R_{26}$, wherein the substituents may be identical or different and are defined as hereinbefore, and unless otherwise specified, the above-mentioned alkyl, alkylene or alkoxy moieties may each contain 1 to 4 carbon atoms, and each carbon atom in the above mentioned alkylene and cycloalkylene moieties is linked to one heteroatom at most;

and the tautomers, stereoisomers and salts thereof.

Particularly preferred compounds of general formula I are those wherein:

X denotes a carbonyl or sulphonyl group;

Y denotes a $CH_2CH_2$, $CH_2CH_2CH_2$, CH=CH, $CH_2CO$ or $COCH_2$ group optionally substituted by one or two methyl groups, or a CO—NH, CH=N or N=CH group optionally substituted by $R_c$;

a first of the groups $R_a$ to $R_c$ denotes an A-B- group wherein

A denotes a group of one of the formulae

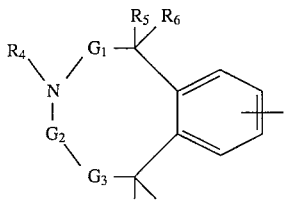

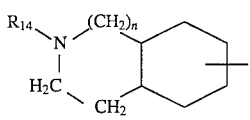

and

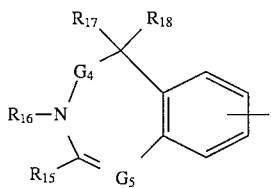

wherein in the benzo moiety of the above-mentioned groups one or two methine groups may each be replaced by a nitrogen atom, $G_1$ denotes a bond or a methylene group,
$G_2$ denotes a bond,
$G_3$ denotes a methylene group,
$G_4$ denotes a bond,
$G_5$ denotes a nitrogen atom or a methine group,
$R_2$ denotes a hydrogen atom,
$R_3$ denotes a hydrogen atom,
$R_4$ denotes a hydrogen atom, a cyclopropyl or cyclopropylmethyl group, a $C_{1-6}$-alkyl group, or an allyl, hydroxyalkyl, carboxyalkyl, alkoxycarbonylalkyl or benzyl group,
$R_5$ denotes a hydrogen atom,
$R_6$ denotes a hydrogen atom,
$R_{14}$ denotes a hydrogen atom or an alkyl group,
$R_{15}$ denotes a hydrogen atom or an alkyl group,
$R_{16}$ denotes a hydrogen atom or an alkyl group,
$R_{17}$ denotes a hydrogen atom or $R_{16}$ together with $R_{17}$ may denote another bond,
$R_{18}$ denotes a hydrogen atom or, if $R_{16}$ and $R_{17}$ together denote another bond, $R_{18}$ may denote an amino group,
n represents the number 1 or 2, and
B denotes a bond or a phenylene group;

a second of the groups $R_a$ to $R_c$ denotes a group of formula

F—E—D— wherein

D denotes an alkylene group,
or a phenylene group,
or a cyclohexylene group,
or a piperidinylene group, wherein the ring nitrogen atom is linked to an optionally substituted straight chain alkylene group of group E,
or a bond,
E denotes a straight chain alkylene group which may be substituted by an alkyl or phenyl group,
or a $C_{2-4}$-alkenylene group,
or a phenylene group,
or, if D does not represent a bond, E may denote a straight chain 0-alkylene group linked to group D via the oxygen atom, and
F denotes a carbonyl group substituted by a hydroxy or alkoxy group, and the shortest distance between the group F and the nitrogen atom of group A-B- which is furthest from the group F is at least 11 bonds, and the third of the groups $R_a$ to $R_c$ denotes a hydrogen atom, an alkoxy group (which alkoxy group may not be bound to a nitrogen atom), or an alkyl or phenyl group;

whilst unless otherwise specified the above mentioned alkyl, alkylene or alkoxy moieties may each contain 1 to 4 carbon atoms and each carbon atom in the above mentioned alkylene and cycloalkylene moieties is linked to 1 heteroatom at most;

and the tautomers, stereoisomers and salts thereof.

Most particularly preferred compounds of general formula I are those wherein

X denotes a carbonyl group,
Y denotes a $CH_2CH_2$, $CH_2CH_2CH_2$, $CH=CH$, $CH_2CO$ or $COCH_2$ group,
or an optionally methyl-substituted $N=CH$ group; the group $R_a$ denotes an A-B group wherein
A denotes a group of one of the formulae

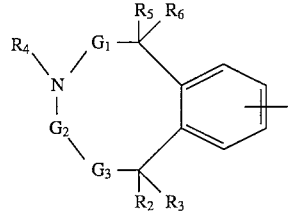

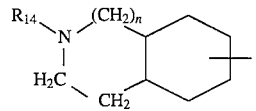

and

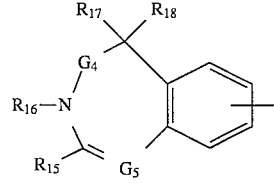

wherein in the benzo moiety of the above-mentioned groups one or two methine groups may each be replaced by a nitrogen atom, $G_1$ denotes a bond or a methylene group,
$G_2$ denotes a bond,
$G_3$ denotes a methylene group,
$G_4$ denotes a bond,
$G_5$ denotes a methine group,
$R_2$ denotes a hydrogen atom,
$R_3$ denotes a hydrogen atom,
$R_4$ denotes a hydrogen atom, a $C_{1-4}$-alkyl group, or an allyl or benzyl group,
$R_5$ denotes a hydrogen atom,
$R_6$ denotes a hydrogen atom,
$R_{14}$ denotes a hydrogen atom or a methyl group, $R_{15}$ denotes a hydrogen atom, $R_{16}$ together with $R_{17}$ denotes a bond, $R_{18}$ denotes a hydrogen atom or an amino group, and n represents the number 1, B denotes a bond;

the group $R_b$ denotes a group of the formula

F—E—D— wherein

D denotes a $CH_2CH_2$ group, or a 1,4-phenylene group, or or a 1,4-cyclohexylene group, E denotes an optionally methyl-substituted $CH_2CH_2$ group, a CH=CH, 1,4-phenylene or O—$CH_2$— group, wherein the oxygen atom of the O—$CH_2$— group is linked to the group D, and F denotes a carbonyl group substituted by a hydroxy or $C_{1-4}$-alkoxy group;

and the shortest distance between the group F and the nitrogen atom of group A-B- which is furthest from group F is at least 11 bonds;

and the tautomers, the stereoisomers and the salts thereof.

The following are mentioned as examples of particularly preferred compounds:

(a) 1-[4-[2-(methoxycarbonyl)ethyl]phenyl]-3-(1,2,3,4-tetrahydroisoquinolin-6-yl)-imidazolidin-2-one, (b) 1-[4-(2-carboxyethyl)phenyl]-3-(1,2,3,4-tetrahydroisoquinolin-6-yl)-imidazolidin-2-one, (c) 1-[4-(2-carboxyethyl)phenyl]-3-(2-methyl-1,2,3,4-tetrahydroisoquinolin-6-yl)-imidazolidin-2-one, (d) 1-[4-[2-(isobutyloxycarbonyl)ethyl]phenyl]-3-(1,2,3,4-tetrahydroisoquinolin-6-yl)imidazolidine-2-one, (e) 1-[4-(2-carboxyethyl)phenyl]-3-(2,3,4,5-tetrahydro-1H-3-benzazepin-7-yl)-imidazolidin-2-one, (f) 1-[4-[2-(methoxycarbonyl)ethyl]phenyl]-3-(2,3,4,5-tetrahydro-1H-3-benzazepin-7-yl)imidazolidin-2-one, (g) 1-[4-[2-(isopropyloxycarbonyl)ethyl]phenyl]-3-(2,3,4,5-tetrahydro-1H-3-benzazepin-7-yl)imidazolidin-2-one, (h) 1-[4-(2-carboxyethyl)phenyl]-3-(3-methyl-2,3,4,5-tetrahydro-1H-3-benzazepin-7-yl)imidazolidin-2-one, (i) 4-[4-[2-(carboxyethyl)phenyl]-5-methyl-2-(2,3,4,5-tetrahydro-1H-3-benzazepin-7-yl)-4H-1,2,4-triazol-3-one, (j) 1-[trans-4-(2-carboxyethyl)cyclohexyl]-3-(2,3,4,5-tetrahydro-1H-3-benzazepin-7-yl)imidazolidin-2-one, (k) 1-[4-[2-(methoxycarbonyl)ethyl]phenyl]-3-(3-methyl-2,3,4,5-tetrahydro-1H-3-benzazepin-7-yl)imidazolidin-2-one, (l) 1-[4-[2-(ethoxycarbonyl)ethyl]phenyl]-3-(3-methyl-2,3,4,5-tetrahydro-1H-3-benzazepin-7-yl)imidazolidin-2-one, (m) 1-[4-[2-(isopropyloxycarbonyl)ethyl]phenyl]-3-(3-methyl-2,3,4,5-tetrahydro-1H-3-benzazepin-7-yl)imidazolidin-2-one, (n) 1-[trans-4-(2-carboxyethyl)cyclohexyl]-3-(3-methyl-2,3,4,5-tetrahydro-1H-3-benzazepin-7-yl)imidazolidin-2-one, (o) 1-[trans-4-[2-(isopropyloxycarbonyl)ethyl]cyclohexyl]-3-(3-methyl-2,3,4,5-tetrahydro-1H-3-benzazepin-7-yl)-imidazolidine-2-one, (p) 1-[trans-4-[2-(ethoxycarbonyl)ethyl]cyclohexyl]-3-(3-methyl-2,3,4,5-tetrahydro-1H-3-benzazepin-7-yl)-imidazolidin-2-one, (q) 1-[trans-4-[2-(methoxycarbonyl)ethyl]cyclohexyl]-3-(3-methyl-2,3,4,5-tetrahydro-1H-3-benzazepin-7-yl)-imidazolidin-2-one, (r) 1-[trans-4-[(carboxymethyl)oxy]cyclohexyl]-3-(3-methyl-2,3,4,5-tetrahydro-1H-3-benzazepin-7-yl)imidazolidin-2-one, (s) 3-[trans-4-(2-carboxyethyl)cyclohexyl]-1-(3-methyl-2,3,4,5-tetrahydro-1H-3-benzazepin-7-yl)hydantoin and (t) 1-[trans-4-(2-carboxyethyl)cyclohexyl]-3-(3-ethyl-2,3,4,5-tetrahydro-1H-3-benzazepin-7-yl)imidazolidin-2-one, and the tautomers and the salts thereof.

According to the invention, the new compounds of general formula I may be obtained, for example, by the following methods:

a) to prepare compounds of general formula I wherein F denotes a carboxyl group:

conversion of a compound of general formula

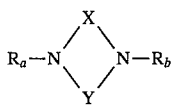
(II)

(wherein $R_a$, $R_b$, X and Y are as hereinbefore defined, with the proviso that one of the groups $R_a$ to $R_d$ denotes an F'-E-D group, wherein E and D are as hereinbefore defined, and F' represents a group which can be converted into a carboxyl group by hydrolysis, treatment with acids, thermolysis or hydrogenolysis)

into a compound of general formula I wherein F denotes a carboxyl group.

For example, functional derivatives of a carboxyl group such as unsubstituted or substituted amides, esters, thioesters, trimethylsilylesters, orthoesters, iminoesters, amidines or anhydrides, or nitrile groups may be converted by hydrolysis into a carboxyl group, esters with tertiary alcohols, e.g. tert.butylesters, may be converted by treatment with an acid or thermolysis into a carboxyl group and esters with aralkanols, e.g. benzylesters, may be converted by hydrogenolysis into a carboxyl group. The hydrolysis is appropriately carried out either in the presence of an acid such as hydrochloric, sulphuric, phosphoric, trichloroacetic or trifluoroacetic acid, or mixtures thereof, in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane, at temperatures between −10° C. and 120° C., e.g. at temperatures between ambient temperature and the boiling temperature of the reaction mixture.

Under the reaction conditions mentioned hereinbefore, any N-acylamino or N-acylimino groups present such as an N-trifluoroacetylimino group may be converted into the corresponding amino or imino groups. Furthermore, any alcoholic hydroxy groups present during the treatment with an organic acid such as trichloroacetic acid or trifluoroacetic acid may simultaneously be converted into a corresponding acyloxy group such as a trifluoroacetoxy group.

If F' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If F' in a compound of formula II represents a tert.butyloxycarbonyl group for example, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, diethylether, tetrahydrofuran or dioxane, preferably at temperatures between −10° C. and 120° C., e.g. at temperatures between 0 and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C. Under the reaction conditions mentioned hereinbefore, any N-tert.butyloxycarbonylamino or N-tert.butyloxycarbonylimino groups present may be converted into the corresponding amino or imino groups.

If F' in a compound of formula II represents a benzyloxycarbonyl group for example, the benzyl group may also be hydrogenolytically cleaved in the presence of a hydrogenation catalyst, such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may also be reduced at the same time, e.g. a nitro group may be reduced to an amino group or a benzyloxy group to a hydroxy group, and an N-benzylamino, N-benzylimino, N-benzyloxycarbonylamino or N-benzyloxycarbonylimino group may be converted into a corresponding amino or imino group.

b) In order to prepare compounds of general formula I wherein $R_{16}$ and $R_{17}$ together represent another bond, $G_4$ denotes a bond and at least one of the groups $R_{15}$ or $R_{18}$ denotes a hydroxy, methoxy, amino, alkylamino or dialkylamino group having 1 to 4 carbon atoms in the alkyl moiety:

reacting a compound of general formula

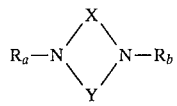 (III)

(wherein
$R_a$, $R_b$, X and Y are hereinbefore defined, with the proviso that one of the groups $R_a$ to $R_d$ denotes an A-B group wherein
B is defined as hereinbefore and
A denotes a group of the formula

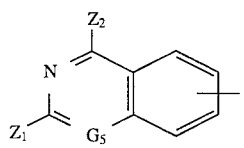

wherein the benzo moiety and $G_5$ are as hereinbefore defined,
$Z_1$ and $Z_2$, which may be identical or different, each denote a nucleophilic leaving group such as a halogen atom, eg. a chlorine or bromine atom, but the group $Z_1$ may also have the meanings given for $R_{15}$ hereinbefore or the group $Z_2$ may have the meanings given for $R_{18}$ hereinbefore)

with a compound of general formula

—$R_{27}$ (IV)

wherein $R_{27}$ denotes a hydroxy, methoxy, amino, formylamino, acetylamino, alkylamino or dialkylamino group having 1 to 4 carbon atoms in the alkyl moiety.

The reaction is expediently carried out in a solvent such as water, acetone, ethanol, tetrahydrofuran, dioxane, dimethylformamide or dimethylsulfoxide, but optionally in an excess of the compound of general formula IV used as solvent and optionally in the presence of a base such as sodium hydroxide, potassium hydroxide, potassium carbonate, sodium amide or sodium hydride at temperatures between 0° and 250° C., but preferably at temperatures between 50° and 225° C.

c) In order to prepare compounds of general formula I wherein $R_{16}$ and $R_{17}$ together denote another bond, $G_4$ denotes a bond and $R_{18}$ denotes a chlorine or bromine atom:

reacting a compound of general formula

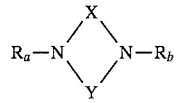 (V)

(wherein
$R_a$, $R_b$, X and Y are as hereinbefore defined, with the proviso that one of the groups $R_a$ to $R_d$ represents an A-B group wherein
B is as hereinbefore defined and
A denotes a group of formula

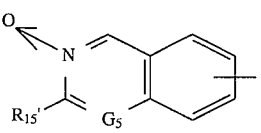

wherein the benzo moiety and $G_5$ are as hereinbefore defined and
$R_{15}'$ denotes a hydrogen atom or represents the alkyl and aryl groups mentioned for $R_{15}$ hereinbefore) with an acid halide.

The reaction is carried out with an acid halide such as phosphorus oxychloride or phosphorus oxybromide, optionally in the presence of a solvent such as benzene, dichlorobenzene, nitrobenzene, or carbon tetrachloride, and optionally in the presence of a salt of a corresponding hydrohalic acid such as sodium chloride or sodium bromide at elevated temperatures, eg. at temperatures between 50° and 250° C., but preferably at the boiling temperature of the reaction mixture.

d) In order to prepare compounds of general formula I wherein X denotes a cyano-substituted carbimino group or a carbonyl or sulphonyl group and Y denotes a straight chain $C_{2-4}$-alkylene group optionally substituted by $R_c$ or $R_d$, or by $R_c$ and $R_d$:

cyclising a compound of general formula

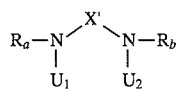 (VI)

wherein
$R_a$ and $R_b$ are as hereinbefore defined, X' denotes a cyano-substituted carbimino group or a carbonyl or sulphonyl group,
one of the groups $U_1$ or $U_2$ denotes a hydrogen atom and the other group $U_1$ or $U_2$ denotes a straight chain $C_{2-4}$-alkylene group optionally substituted by $R_c$ or $R_d$, or by $R_c$ and $R_d$, to which additionally a nucleophilic leaving group such as a halogen atom, a hydroxy or sulphonic acid ester group, eg. a chlorine, bromine or iodine atom or a hydroxy, methanesulfonyloxy or p-toluenesulfonyloxy group) is terminally bound.

The reaction is preferably carried out in a solvent such as methylene chloride, acetonitrile, tetrahydrofuran, toluene, dimethylformamide or dimethylsulfoxide, optionally in the presence of a base such as sodium hydride, potassium carbonate, potassium tert.butoxide or N-ethyl-diisopropylamine or optionally in the presence of a dehydrating agent such as triphenylphosphine/diethyl azodicarboxylate, at temperatures between −20° and 100° C., preferably at temperatures between 0° and 60° C.

e) In order to prepare compounds of general formula I wherein X denotes a carbonyl group and Y denotes one of the above mentioned alkylene or alkenylene groups:

reacting a compound of general formula

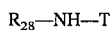

$R_{28}$—NH—T            (VII)

with an isocyanate of general formula

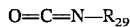

O=C=N—$R_{29}$            (VIII)

(wherein one of the groups $R_{28}$ or $R_{29}$ has the meanings given for $R_a$ hereinbefore and the other group $R_{28}$ or $R_{29}$ has the meanings given for $R_b$ hereinbefore and T denotes a group of the formula

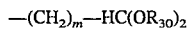

—(CH$_2$)$_m$—HC(OR$_{30}$)$_2$ optionally substituted in the alkylidene moiety by $R_c$ or $R_d$ or by $R_c$ and $R_d$, wherein m denotes the number 1, 2 or 3 and denotes a $C_{1-4}$-alkyl group)

optionally with subsequent hydrogenation.

The reaction is optionally carried out in an inert solvent such as dioxane or toluene at temperatures between 20° and 200° C., preferably at temperatures between 20° and 160° C. However, the reaction can also be carried out without a solvent.

An open-chained urea optionally obtained as an intermediate product in the reaction of a compound of general formula VII with an isocyanate of general formula VIII is, if desired, subsequently converted into the desired compound in the presence of an acid such as acetic acid, trifluoroacetic acid, p-toluenesulphonic acid or hydrochloric acid, optionally in a solvent such as methanol, ethanol, tetrahydrofuran or methylene chloride at temperatures between 0° C. and the boiling temperature of the reaction mixture.

The optional subsequent hydrogenation is preferably carried out with hydrogen in the presence of catalyst such as palladium/charcoal or platinum, in a solvent such as methanol, ethanol, ethyl acetate or glacial acetic acid, optionally with the addition of an acid such as hydrochloric acid, at temperatures between 0° and 100° C., but preferably at temperatures between ambient temperature and 50° C., and under a hydrogen pressure of 1 to 7 bar, but preferably 3 to 5 bar.

f) In order to prepare compounds of general formula I wherein $G_1$ and $G_2$ each represent a bond, $G_3$ represents a methylene group optionally substituted by a $C_{1-4}$-alkyl group, $R_2$, $R_4$ and $R_5$ each represent a hydrogen atom, and $R_3$ and $R_6$, which may be identical or different, each represent a hydrogen atom or a $C_{1-4}$-alkyl group:

hydrogenation of a compound of general formula

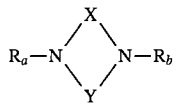

(IX)

wherein $R_a$, $R_b$, X and Y are as hereinbefore defined, with the proviso that one of the groups $R_a$ to $R_d$ denotes an A-B group, wherein B is as hereinbefore defined and A denotes a group of formula

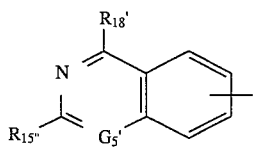

wherein, the benzo moiety is as hereinbefore defined, $G_5'$ denotes a methine group optionally substituted by a $C_{1-4}$-alkyl group, $R_{15}''$ and $R_{18}'$, which may be identical or different, each represent a hydrogen atom or a $C_{1-4}$ alkyl group.

The hydrogenation is preferably carried out in a suitable solvent such as methanol, methanol/water, acetic acid, ethyl acetate, ethanol, ether, tetrahydrofuran, dioxane or dimethylformamide with hydrogen in the presence of a hydrogenation catalyst such as Raney nickel, platinum, platinum dioxide, rhodium or palladium/charcoal, optionally with the addition of an acid such as hydrochloric acid at temperatures between 0° and 100° C., preferably at temperatures between 20° and 80° C. Any optionally substituted alkenylene groups present in a compound of general formula IX may thereby be converted into optionally substituted alkylene groups.

g) In order to prepare compounds of general formula I wherein F denotes a carbonyl group substituted by a $C_{1-6}$-alkoxy group, by an arylalkoxy group (having 1 to 4 carbon atoms in the alkoxy moiety and wherein the aryl moiety is as hereinbefore defined), or by an $R_{22}O$ group:

reacting a compound of general formula

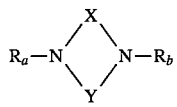

(X)

(wherein $R_a$, $R_b$, X and Y are as hereinbefore defined, with the proviso that one of the groups $R_a$ to $R_d$ denotes an F"-E-D group, wherein E and D are as hereinbefore defined and F" denotes a carboxy or alkoxycarbonyl group)

with an alcohol of general formula

HO—$R_{31}$            (XI)

wherein $R_{31}$ has the meanings given for $R_{22}$ hereinbefore or denotes a $C_{1-6}$-alkyl group or an arylalkyl group in which the aryl moiety is as hereinbefore defined and the alkyl moiety may contain 1 to 4 carbon atoms.

The reaction of a carboxy compound is optionally carried out in a solvent or mixture of solvents such as methylene chloride, dimethylformamide, benzene, toluene, chlorobenzene, tetrahydrofuran, benzene/tetrahydrofuran or dioxane or, particularly advantageously, in a corresponding alcohol of general formula XI, optionally in the presence of an acid such as hydrochloric acid or in the presence of a dehydrating agent, eg. in the presence of isobutyl-chloroformate, tetraethyl orthocarbonate, trimethyl-orthoacetate, 2,2-dimethoxypropane, tetramethoxysilane, thionylchloride, trimethyl-chlorosilane, sulphuric acid, methanesulphonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, N,N'-carbonyldiimidazole or triphenylphosphine/carbon tetrachloride, and optionally with the addition of a base such as pyridine, 4-dimethylaminopyridine or triethylamine, expediently at temperatures between 0° and 150° C., preferably at temperatures between 0° and 100° C.

The reaction of a corresponding alkoxycarbonyl compound with an alcohol of general formula XI is preferably carried out in a corresponding alcohol as solvent, optionally in the presence of a further solvent such as methylene chloride or ether, preferably in the presence of an acid such as hydrocholoric acid at temperatures between 0° and 150° C., preferably at temperatures between 50° and 100° C.

h) In order to prepare compounds of general formula I wherein one of the groups $R_4$, $R_{14}$ or $R_{16}$ represents one of the optionally substituted alkyl, alkenyl, cycloalkyl, cycloalkylalkyl or aralkyl groups mentioned hereinbefore in the definition of groups $R_4$, $R_{14}$ or $R_{16}$:

reacting a compound of general formula

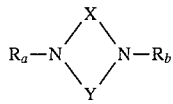

(XII)

(wherein $R_a$, $R_b$, X and Y are as hereinbefore defined, with the proviso that one of the groups $R_a$ to $R_d$ denotes an A-B group, wherein A and B are as hereinbefore defined, with the proviso that $R_4$, $R_{14}$ and $R_{16}$ each represent a hydrogen atom) with a compound of general formula

(XIII)

wherein $R_{32}$ denotes a $C_{1-8}$-alkyl group, a cycloalkyl or cycloalkylalkyl group in which the cycloalkyl moiety may contain 3 to 7 carbon atoms and the alkyl moiety may contain 1 to 4 carbon atoms, a $C_{3-8}$-alkenyl group, or an arylalkyl, hydroxyalkyl, alkoxyalkyl, cyanoalkyl, carboxyalkyl, alkoxycarbonylalkyl, aminocarbonylalkyl, N-alkylaminocarbonylalkyl or N,N-dialkylaminocarbonyl group, wherein the aryl moiety and the alkyl moieties are as hereinbefore defined, and $Z_3$ denotes a nucleophilic leaving group such as a halogen atom, eg. a chlorine, bromine, or iodine atom, or a sulphonic acid ester group, eg. a methanesulphonyloxy or p-toluenesulfonyloxy group, or $Z_3$ together with an adjacent hydrogen atom of the group $R_{32}$ denotes an oxygen atom.

The alkylation with a compound of formula XIII wherein $Z_3$ denotes a nucleophilic leaving group is expediently carried out in a solvent such as methylene chloride, tetrahydrofuran, dioxane, dimethylsulfoxide or dimethylformamide, optionally in the presence of a base such as sodium carbonate, potassium carbonate or sodium hydroxide solution or in the presence of a tertiary organic base such as N-ethyl-diisopropylamine or N-methyl-morpholine, which may simultaneously be used as solvents, at temperatures between −30° and 150° C., but preferably at temperatures between 20° and 120° C.

The reductive alkylation with a carbonyl compound of general formula XIII is carried in the presence of a complex metal hydride such as sodium borohydride, lithium borohydride or sodium cyanoborohydride, expediently at a pH from 6–7 and at ambient temperature or in the presence of a hydrogenation catalyst, eg. with hydrogen in the presence of palladium/charcoal, under a hydrogen pressure of 1–5 bar. However, methylation is preferably carried out in the presence of formic acid as reducing agent at elevated temperatures, eg. at temperatures between 60° and 120° C.

i) In order to prepare compounds of general formula I wherein X represents a carbimino group which is substituted by a cyano group at the nitrogen atom, or X represents a carbonyl or sulphonyl group:

reacting a compound of general formula

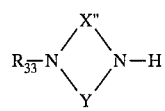

(XIV)

with a compound of general formula

(XV)

(wherein

Y is as hereinbefore defined,

X" denotes a carbimino group substituted by a cyano group at the nitrogen atom, or X" denotes a carbonyl or sulphonyl group, one of the groups $R_{33}$ or $R_{34}$ has the meanings given for $R_a$ hereinbefore and the other group $R_{33}$ or $R_{34}$ has the meanings given for $R_b$ hereinbefore and $Z_4$ denotes a nucleophilic leaving group such as a halogen atom, a hydroxy or sulphonic acid ester group, eg. a fluorine, chlorine, bromine or iodine atom or a methanesulphonyloxy or p-tolunesulfonyloxy group).

The reaction is preferably carried out in a solvent such as methylene chloride, acetonitrile, tetrahydrofuran, toluene, pyridine, dimethylformamide, dimethylsulfoxide or N-methylpyrrolidone, optionally in the presence of one or more bases such as sodium hydride, potassium carbonate, potassium tert.butoxide, N-ethyl-diisopropylamine, tris-[2-(2-methoxyethoxy) ethyl]amine or N,N,N',N'-tetramethylethylenediamine and optionally in the presence of a dehydrating agent such as triphenyl-phosphine/diethyl azodicarboxylate and optionally in the presence of copper powder or one or more copper salts such as copper(I) iodide as reaction accelerators, at temperatures between −20° and 250° C., but preferably at temperatures between 0° and 60° C., if $Z_4$ is bound to an aliphatic carbon atom, or at temperatures between 60° and 180° C., if $Z_4$ is bound to an aromatic carbon atom, whilst in this case $Z_4$ can only represent a halogen atom.

j) In order to prepare compounds of general formula I wherein $R_4$ or $R_{14}$ denotes an alkoxycarbonyl, arylmethyloxycarbonyl, formyl, acetyl, trifluoroacetyl, allyloxycarbonyl or $R_{11}CO-O-(R_{12}CR_{13})-O-CO$ group, wherein $R_{11}$ to $R_{13}$ and the aryl moiety are as hereinbefore defined and the alkoxy moiety may contain 1 to 4 carbon atoms:

reacting a compound of general formula

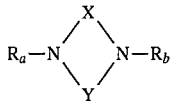 (XVI)

(wherein $R_a$, $R_b$, X and Y are as hereinbefore defined, with the proviso that $R_4$ or $R_{14}$ denotes a hydrogen atom)

with a compound of general formula

 (XVII)

wherein $R_{35}$ represents an alkoxycarbonyl group having a total of 2 to 5 carbon atoms, an arylmethyloxycarbonyl group in which the aryl moiety is as hereinbefore defined, or a formyl, acetyl, allyoxycarbonyl, $R_{11}CO$—$O$—($R_{12}CR_{13}$)—$O$—$CO$ or trifluoroacetyl group, wherein $R_{11}$ to $R_{13}$ are as hereinbefore defined, and $Z_5$ denotes a nucleophilic leaving group such as a halogen atom, or an aryloxy, arylthio, alkoxy, alkoxycarbonyloxy, aralkoxycarbonyloxy or N-imidazolyl group, eg. a chlorine or bromine atom or a 4-nitrophenoxy group.

The acylation is expediently carried out in a solvent such as tetrahydrofuran, methylene chloride, chloroform, dimethylformamide, water or mixtures of these solvents, optionally in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvents, at temperatures between –30° and 100° C., but preferably at temperatures between –10° and 60° C.

k) In order to prepare compounds of general formula I wherein F denotes a carbonyl group which is substituted by a $C_{1-6}$-alkoxy group, by an arylalkoxy group (in which the aryl moiety is defined as hereinbefore and the alkoxy moiety may contain 1 to 4 carbon atoms), or by an $R_{22}O$ or $R_{23}CO$—$O$—$CHR_{24}O$ group, wherein $R_{22}$ to $R_{24}$ are as hereinbefore defined:

reacting a compound of general formula

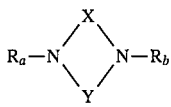 (XVIII)

(wherein $R_a$, $R_b$, X and Y are as hereinbefore defined, with the proviso that one of the groups $R_a$ to $R_d$ denotes an F'''-E-D- group wherein E and D are as hereinbefore defined and F''' denotes a carboxyl group)

with a compound of general formula

 (XIX)

wherein $R_{36}$ represents a $C_{1-6}$-alkyl group, an arylalkyl group (in which the aryl moiety is defined as hereinbefore and the alkyl moiety may contain 1 to 4 carbon atoms), or $R_{22}$— or $R_{23}CO$—$O$—$CHR_{24}$— group (wherein $R_{22}$ to $R_{24}$ are as hereinbefore defined), and $Z_6$ denotes a nucleophilic leaving group such as a halogen atom or a sulphonic acid ester group, eg. a chlorine or bromine atom or a methanesulphonyloxy or p-toluenesulphonyloxy group.

The reaction is preferably carried out in a solvent such as methylene chloride, tetrahydrofuran, dioxane, dimethylsulfoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methylmorpholine, which may simultaneously serve as solvents, or optionally in the presence of silver carbonate or silver oxide, at temperatures between –30° and 100° C., but preferably at temperatures between –10° and 80° C.

l) In order to prepare compounds of general formula I wherein X denotes a carbonyl group and Y denotes a straight chain $C_{2-4}$-alkylene group which is optionally substituted by $R_c$ or $R_d$, or by $R_c$ and $R_d$ and in which a methylene group in the terminal position is replaced by a carbonyl group:

cyclising a compound of general formula

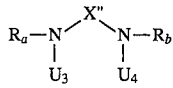 (XX)

(wherein $R_a$ $R_b$ are ad hereinbefore defined,

X" denotes a carbonyl group, one of the groups $U_3$ or $U_4$ represents a hydrogen atom and the other group $U_3$ or $U_4$ represents a straight chain $C_{2-4}$-alkylene group which is optionally substituted by $R_c$ or $R_d$, or by $R_c$ and $R_d$, and in which a terminal methylene group is replaced by a $Z_7$—CO group, wherein $Z_7$ represents a nucleophilic leaving group such as a halogen atom or a hydroxy, alkoxy, aryloxy or arylalkoxy group, eg. a chlorine or bromine atom or a hydroxy, methoxy, ethoxy, phenoxy or benzyloxy group), optionally formed in the reaction mixture.

The reaction is preferably carried out in a solvent such as methylene chloride, acetonitrile, tetrahydrofuran, toluene, dimethylformamide or dimethylsulfoxide, optionally in the presence of a base such as sodium hydride, potassium carbonate, potassium tert.butoxide or N-ethyl diisopropylamine or optionally in the presence of a dehydrating agent such as triphenylphosphine/diethyl azodicarboxylate or N,N'-carbonyldiimidazole, at temperatures between –20° and 200° C., preferably at temperatures between 0° and 160° C.

If according to the invention a compound of general formula I is obtained which contains an unsaturated carbon-carbon bond, this may be converted by catalytic hydrogenation into a corresponding saturated compound of general formula I.

The catalytic hydrogenation is preferably carried out with hydrogen in the presence of a catalyst such as palladium/charcoal, in a solvent such as methanol, ethanol, ethyl acetate or glacial acetic acid, optionally with the addition of an acid such as hydrochloric acid at temperatures between 0° and 100° C., but preferably at temperatures between 20° and 60° C., and under a hydrogen pressure of 1 to 7 bar, but preferably 3 to 5 bar.

In the reactions described hereinbefore, any reactive groups present such as hydroxy, carboxy, phosphono, amidino, O-alkylphosphono, amino, alkylamino, imino or amidino groups may be protected during the reaction by means of conventional protecting groups which are cleaved again after the reaction.

For example, the protecting group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting group for a phosphono group may be an alkyl group such as a methyl, ethyl, isopropyl or n-butyl, phenyl or benzyl group, the protecting group for an optionally alkyl substituted amidino group may be a benzyloxycarbonyl group and the protecting group for an amino, alkylamino or imino group may be a formyl, acetyl, trifluoroacetyl, ethoxycarbonyl, tert.-butoxycarbonyl, benzyloxycarbonyl, benzyl, methoxybenzyl or 2,4-dimethoxy benzyl group, and for an imino group a methyl group is also possible and for an amino group a phthalyl group may also be considered.

The optional subsequent cleaving of a protecting group may, for example, be carried out hydrolytically in an aqueous solvent, e.g. in water, isopropanol/water, acetic acid/ water, tetrahydrofuran/water or dioxane/water, in the presence of an acid such as trifluoroacetic acid, hydrochloric acid, or sulphuric acid or in the presence of an alkali metal base such as sodium hydroxide or potassium hydroxide, or by ether cleavage, e.g. in the presence of iodotrimethylsilane, at temperatures between 0° and 120° C., preferably at temperatures between 10° and 100° C.

However, a benzyl, methoxybenzyl or benzyloxycarbonyl group may be cleaved hydrogenolytically, for example, using hydrogen in the presence of a catalyst such as palladium/charcoal, in a solvent such as methanol, ethanol, ethyl acetate or glacial acetic acid, optionally with the addition of an acid such as hydrochloric acid, at temperatures between 0° and 100° C., but preferably between 20° and 60° C., under a hydrogen pressure of 1 to 7 bar, preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic or hydrochloric acid, or by treating with iodotrimethylsilane, optionally using a solvent such as methylene chloride, dioxane, methanol or ether.

A trifluoroacetyl group is preferably cleaved by treating with an acid such as hydrochloric acid, optionally in the presence of a solvent such as acetic acid or methanol, at temperatures between 50° and 120° C. or by treating with sodium hydroxide solution, optionally in the presence of a solvent such as tetrahydrofuran or methanol, at temperatures between 0° and 50° C.

The cleaving of a methyl group from a methylimino group is preferably carried out in the presence of 1-chloroalkylchloroformates such as 1-chloroethyl chloroformate, preferably in the presence of a base such as 1,8-bis-(dimethylamino)-naphthalene in the presence of a solvent such as methylene chloride, 1,2-dichloroethane, toluene or dioxane, at temperatures between 0° and 150° C., preferably at temperatures between 20° C. and the boiling temperature of the reaction mixture, and subsequently treating with an alcohol such as methanol, at temperatures between 20° C. and the boiling temperature of the alcohol used.

A phthalyl group is preferably cleaved in the presence of hydrazine or a primary amine such as methylamine, ethylamine or n-butylamine, in a solvent such as methanol, ethanol, isopropanol, toluene/water or dioxane, at temperatures between 20° and 50° C.

The cleaving of only one alkyl group from an O,O'-dialkylphosphono group is preferably carried out using sodium iodide, in a solvent such as acetone, ethylmethylketone, acetonitrile or dimethylformamide, at temperatures between 40° and 150° C., but preferably at temperatures between 60° and 100° C.

The cleaving of both alkyl groups from an O,O'-dialkylphosphono group is carried out, for example, with iodotrimethylsilane, bromotrimethylsilane or chlorotrimethylsilane/sodium iodide in a solvent such as methylene chloride, chloroform or acetonitrile, at temperatures between 0° C. and the boiling temperature of the reaction mixture, but preferably at temperatures between 20° and 60° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (see. Allinger N. L. and Eliel E. L. in "Topics in Stereochemistry", Vol. 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance, especially an acid or an activated derivative thereof or an alcohol, which forms salts or derivatives such as esters or amides with the racemic compound, and separation of the diastereomeric salt mixture or derivative thus obtained, e.g. on the basis of their different solubilities, whilst the free antipodes may be released from the pure diastereomeric salts by the action of suitable agents. Particularly common, optically active acids include, for example, the D- and L-forms of tartaric and dibenzoyltartaric acid, di-o-tolyl-tartaric acid, malic acid, mandelic acid, camphorsulphonic acid, glutamic acid, aspartic acid or quinic acid. Examples of an optically active alcohol include (+) or (−)-menthol and examples of an optically active acyl group in amides include (+) or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compounds of formula I thus obtained, if they contain a carboxyl, sulpho, phosphono, O-alkyl-phosphono or tetrazol-5-yl group, may subsequently, if desired, be converted into the addition salts thereof with inorganic or organic bases, more particularly for pharmaceutical use, into the physiologically acceptable addition salts thereof. Examples of suitable bases include sodium hydroxide, potassium hydroxide, arginine, cyclohexylamine, ethanolamine, diethanolamine and triethanolamine.

The compounds used as starting materials are known from the literature in some cases or may be obtained by methods known from the literature (see the Examples).

Thus, for example, "The Organic Chemistry of Heterocyclic Compounds", volume 37, by C. Temple Jr., published by John Wiley & Sons, 1981, describes in Chapters 13, 14 and 19 the preparation of corresponding triazole compounds.

In Houben-Weyl, "Methoden der Organischen Chemie", volume E4, by H. Hagemann, Georg Thieme Verlag, 1983, there is a description on page 368 onwards of the preparation of corresponding cyclic urea compounds. Also, in the same volume, pages 355 onwards, there is a description by way of example of the preparation of corresponding open-chained urea compounds possibly needed as starting compounds.

Thus, for example, a corresponding cyclic urea derivative is obtained by cyclising a correspondingly substituted urea (which is in turn obtained by reacting a corresponding amine with a corresponding isocyanate), or by reacting a correspondingly substituted diamine with a carbonic acid derivative such as phosgene, or a corresponding triazolone derivative is obtained by cyclising a corresponding semicarbazide, which is in turn obtained by reacting a corresponding isocyanate with a corresponding hydrazide.

In the cyclic urea derivatives thus obtained, a carbonyl group can subsequently, if desired, be converted into a corresponding thiocarbonyl or carbimino group using known methods.

In the resulting cyclic starting compounds or in the starting compounds required to prepare them, any ester group present can be converted by hydrolysis into a carboxyl group or any carboxyl group present can be converted into an ester group.

As already mentioned, the new cyclic derivatives of general formula I and the addition salts thereof, particularly the physiologically acceptable addition salts thereof with inorganic or organic acids or bases, have valuable properties. Thus, the compounds of general formula I have valuable pharmacological properties and in addition to having an inhibitory effect on inflammation and bone degradation, have, in particular, antithrombotic, antiaggregatory and tumour- or metastasis-inhibiting effects.

By way of example, the compounds of general formula I were investigated for their biological effects as follows:

1. Inhibition of the binding of $^3$H-BIBU 52 to Human thrombocytes

A suspension of human thrombocytes in plasma is incubated with $^3$H-BIBU 52 [=(3S,5S)-5-[(4'-amidino-4-biphenylyl)oxymethyl]-3-[(carboxy)methyl]-2-pyrrolidinone[3-$^3$H-4-biphenylyl]], which replaces the ligand $^{125}$I-fibrinogen known from the literature (see German Patent Application P 42 14 245.8 by the same applicant dated Apr. 4, 1992, internal reference number: Case 5/1093-FL) and various concentrations of the test substance. The free and bound ligand are separated by centrifuging and quantitatively measured by scintillation counting. From the measurements obtained the inhibition of $^3$H-BIBU 52 binding caused by the test substance is determined.

In order to do this, donor blood is taken from an anticubital vein and anti-coagulated with trisodium citrate (final concentration 13 mM). The blood is centrifuged for 10 minutes at 170× g and the supernatant platelet-rich plasma (PRP) is removed. The remaining blood is centrifuged vigorously once more in order to recover plasma. The PRP is diluted with autologous plasma 1:10. 750 µl are incubated for 20 minutes at ambient temperature with 50 µl of physiological saline solution, 100 µl of test substance solution, 50 µl of $^{14}$C-sucrose (3700 Bq) and 50 µl of $^3$H-BIBU 52 (final concentration: 5 nM). In order to measure the non specific binding, 5 µl of BIBU 52 (final concentration 30 µM) are used instead of the test substance. The samples are centrifuged for 20 seconds at 10000× g and the supernatant is drawn off. 100 µl thereof are measured in order to determine the free ligand. The pellet is dissolved in 500 µl of 0.2N NaOH, 450 µl are mixed with 2 ml of scintallator and 25 µl of 5N HCl, and measured. The residual plasma remaining in the pellet is determined from the $^{14}$C-content, and the bound ligand is determined from the $^3$H-measurement. After subtracting the non specific binding, the pellet activity is plotted against the concentration of the test substance and the concentration for 50% inhibition of binding is determined.

2. Antithrombotic activity

Method

Thrombocyte aggregation is measured using the Born and Cross method (J. Physiol. 170:397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of the aggregation-triggering substance. The rate of aggregation is determined from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used.

Before the addition of the collagen the plasma is incubated for 10 minutes with the test substance at 37° C.

From the measurements obtained, an $EC_{50}$ is determined graphically, indicating a 50% change in the optical density in terms of the inhibition of aggregation.

The Table which follows contains the results found:

| Substance (Example No.) | $^3$H-BIBU 52-binding test $IC_{50}$ [nM] | Inhibition of platelet aggregation $EC_{50}$ [nM] |
|---|---|---|
| 1 | 190 | >10000 |
| 2(1) | 5400 | >10000 |
| 2(2) | 24 | 40 |
| 6 | 110 | 40 |
| 8(1) | 36 | 150 |
| 9 | 85 | 190 |
| 9(1) | 760 | 990 |
| 19 | 59 | 230 |
| 19(1) | 120 | 350 |
| 19(3) | 81 | 430 |

Moreover, the compounds of Examples 7 and 19, for example, inhibit the collagen-induced thrombocyte aggregation ex vivo in Rhesus monkeys for more than 5 and more than 8 hours, respectively, after oral administration of 1 mg/kg.

The compounds according to the invention are well tolerated because after intravenous administration of 30 mg/kg of the compounds of Examples (8)1 and 19 to three mice, none of the three test animals died.

In the light of their inhibitory effect on cell-cell and cell-matrix interactions, the new cyclic urea derivatives of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 µg and 30 mg/kg of body weight, preferably 1 µg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatan sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

EXAMPLE I 1-(Isoquinolin-N-oxide-6-yl)-3-[4 -[2-(methoxycarbonyl)-ethyl]-phenyl]-imidazolidin-2-one 2.6 g of 1-(isoquinolin-6-yl)-3-[4-[2-(methoxycarbonyl)-ethyl]-phenyl]-imidazolidin-2-one are dissolved in 175 ml of methylene chloride with heating. The mixture is cooled in an ice bath and mixed with 1.46 g of 3-chloroperoxybenzoic acid (90% strength). After 24 hours stirring at 0° C. the mixture is diluted with methylene chloride and extracted twice with sodium hydrogen carbonate and sodium thiosulphate solution and then with water. The organic phase is separated off, dried and evaporated down.

Yield: 2.4 g (88% of theory), $R_f$ value: 0.15 (silica gel; methylene chloride/methanol/ethyl acetate=20:1:1)

EXAMPLE II

N-(2-Hydroxyethyl)-N'-(isoquinolin-6-yl)-N-[4-[2-(methoxycarbonyl)ethyl]phenyl]-urea To 7.2 g of imidazole and 10.1 g of N,N'-carbonyldiimidazole in 100 ml of dimethylformamide are added dropwise, at a temperature of 0° to 10° C., 9.0 g of 6-aminoisoquinoline in 70 ml of dimethylformamide. After 2 hours stirring at ambient temperature, 15.3 g of N-(2-hydroxyethyl)-4-[2-(methoxycarbonyl)ethyl]-aniline in 20 ml of dimethylformamide are added dropwise and the mixture is stirred for 2 ½ days at ambient temperature. The mixture is diluted with 750 ml of ethyl acetate and extracted twice with water and saturated saline solution. The organic phase is separated off, dried and evaporated down. The residue is purified by chromatography over a silica gel column using ethyl acetate/methylene chloride/methanol=70:30:10.

Yield: 4.8 g (19% of theory), $R_f$ value: 0.48 (silica gel; methylene chloride/methanol/ethyl acetate=20:1:1)

The following compounds are obtained analogously to Example II:

(1) N-(2,2-diethoxyethyl)-N'-(isoquinolin-6-yl)-N-[4-[2-(methoxycarbonyl)ethyl]phenyl]-urea $R_f$ value: 0.50 (silica gel; methylene chloride/methanol=20:1)

(2) N-(3-ethyl-2,3,4,5-tetrahydro-1H-3-benzazepin-7-yl)N'-(2,2-diethoxyethyl)-N'-[trans-4-[2-(methoxycarbonyl)ethyl]-cyclohexyl]-urea Melting point: 101°–104° C.

$R_f$ value: 0.63 (silica gel; methylenechloride/methanol/conc. aqueous ammonia=90:10:2)

(3) N-(7-ethyl-6,7,8,9-tetrahydro-5H-pyrazino[2,3-d]azepin-2-yl)-N'-(2,2-diethoxyethyl)-N'-[trans-4-[2-(methoxycarbonyl)-ethyl]cyclohexyl]-urea Carried out with 1,1'-carbonyl-di-(1,2,4-triazole)

Melting point: 100°–102° C.

$R_f$ value: 0.41 (silica gel; methylene chloride/methanol =9:1)

Calc.: C 62.40 H 8.73 N 13.48 Found: 62.19 8.79 13.62

(4) N-(7 -benzyl-6,7,8,9-tetrahydro-5H-pyrimido-[-4,5-d]azepin-2-yl)-N'-(2,2-diethoxyethyl)-N'-[trans-4-[2-(methoxycarbonyl)-ethyl]cyclohexyl]-urea Carried out with 1,1'-carbonyl-di-(1,2,4-triazole)

$R_f$ value: 0.23 (Reversed Phase silica gel; methanol/5% aqueous saline solution=6:4)

EXAMPLE III

N-(3-tert. Butyloxycarbonyl-2,3,4,5-tetrahydro-1H-3-benzazepin-7-yl)-N-(2-hydroxyethyl)-N'-[4-[2-(methoxycarbonyl)ethyl]-phenyl]-urea 4.5 g of 3-(tert.butyloxycarbonyl)-7-[(2-hydroxyethyl)amino]-2,3,4,5-tetrahydro-1H-3-benzazepine and 3.7 g of 4-[2-(methoxycarbonyl)ethyl]-phenylisocyanate (prepared from the corresponding amine by reaction with phosgene) are stirred in 35 ml of dioxane for 3.5 hours at ambient temperature. The reaction mixture is evaporated down, the residue is triturated with tert.butylmethylether and suction filtered. The product is washed with tert.butyl-methylether and dried. Yield: 6.3 g (76% of theory), Melting point: 115°–117° C., $R_f$ value: 0.30 (silica gel; cyclohexane/ethyl acetate=1:1)

The following compounds are obtained analogously to Example III:

(1) 1-acetyl-4-[4-[2-(methoxycarbonyl)ethyl]phenyl]-semicarbazide (Reaction of acetylhydrazine with 4-[2-(methoxycarbonyl)-ethyl]-phenylisocyanate)

Melting point: 159°–165° C.

$R_f$ value: 0.37 (silica gel; methylene chloride/methanol=9:1)

(2) N-(2-hydroxyethyl)-N-[trans-4-[2-(methoxycarbonyl)-ethyl]-cyclohexyl]-N'-(3-trifluoroacetyl-2,3,4,5-tetrahydro-1H-3-benzazepin-7-yl)-urea Melting point: 150°–152 ° C.

$R_f$ value: 0.31 (silica gel; cyclohexane/ethyl acetate=1:1)

(3) N-(2,2-diethoxyethyl)-N-(3-trifluoroacetyl-2,3,4,5-tetrahydro-1H-3-benzazepin-7-yl)-N'-[trans-4-[2-(methoxycarbonyl)-ethyl]-cyclohexyl]-urea The [trans-4-[2-(methoxycarbonyl)ethyl]cyclohexyl]isocyanate used is obtained from the corresponding amine-hydrochloride by reaction with phosgene. The 7-[(2,2-diethoxyethyl)amino]-3-trifluoroacetyl-2,3,4,5-tetrahydro-1H-3-benzazepine used [

R$_f$ value: 0.76 (silica gel; cyclohexane/ethyl acetate=3:2)] is obtained by reacting 7-amino-3-trifluoroacetyl-2,3,4,5-tetrahydro-1H-3-benzazepine with bromoacetaldehyde-diethylacetal in the presence of N-ethyl-diisopropylamine.

R$_f$ value: 0.26 (silica gel; cyclohexane/ethyl acetate=3:2)
(4) N-[trans-[[(methoxycarbonyl)methyl]oxy]cyclohexyl]-N'-(2,2-diethoxyethyl)-N'-(3-trifluoroacetyl-2,3,4,5-tetrahydro-1H-3-benzazepin-7-yl)-urea The [trans-4-[[(methoxycarbonyl)methyl]oxy]cyclohexyl]-isocyanate used is obtained from the corresponding amine hydrochloride by reaction with phosgene.

R$_f$ value: 0.20 (silica gel; cyclohexane/ethyl acetate=1:1)
(5) N-(2-hydroxyethyl)-N-[4-[trans-2-(methoxycarbonyl)ethenyl]phenyl]-N'-(3-trifluoroacetyl-2,3,4,5-tetrahydro-1H-3-benzazepin-7-yl)-urea The (3-trifluoroacetyl-2,3,4,5-tetrahydro-1H-3-benzazepin-7-yl)-isocyanate used is obtained from the corresponding amine by reaction with phosgene.

Melting point: from 118° C.

R$_f$ value: 0.18 (silica gel; cyclohexane/ethyl acetate=1:1)
(6) N-[4-(2-(ethoxycarbonyl)-1-propyl]phenyl]-N'-(2,2-diethoxyethyl)-N'-(3-trifluoroacetyl-2,3,4,5-tetrahydro-1H-3-benzazepin-7-yl)-urea The [4-2-(ethoxycarbonyl)-1-propyl]phenyl]-isocyanate used is obtained by reacting the corresponding amine with phosgene.

R$_f$ value: 0.35 (silica gel; cyclohexane/ethyl acetate=2:1)
(7) N-[trans-4-[2-(methoxycarbonyl)ethyl]cyclohexyl]-N'-[(benzyloxycarbonyl)methyl]-N'-(3-trifluoroacetyl-2,3,4,5-tetrahydro-1H-3-benzazepin-7-yl)-urea The 7-[[(benzyloxycarbonyl)methyl]amino]-3-trifluoroacetyl-2,3,4,5-tetrahydro-1H-3-benzazepine used [R$_f$ value: 0.24 (silica gel; cyclohexane/ethyl acetate=4:1)]is obtained by reacting 7-amino-3-trifluoroacetyl-2,3,4,5-tetrahydro-1H-3-benzazepine with benzyl bromoacetate in the presence of N-ethyl-diisopropylamine.

R$_f$ value: 0.51 (silica gel; cyclohexane/ethyl acetate=1:1)
(8) N-(3-hydroxypropyl)-N-[trans-4-[2-(methoxycarbonyl)ethyl]cyclohexyl]-N'-(3-trifluoroacetyl-2,3,4,5-tetrahydro-1H-3-benzazepin-7-yl)-urea Melting point: 129°–130° C.
(9) 1-acetyl-4-[trans-4-[2-(methoxycarbonyl)ethyl]cyclohexyl]-semicarbazide Melting point: 176°–179° C.

R$_f$ value: 0.24 (silica gel; methylene chloride/methanol =95:5)
(10) 1-formyl-4-[trans-4-[2-(methoxycarbonyl)ethyl]cyclohexyl]-semicarbazide Melting point: 169°–171° C.
(11) N-[4-[2-(ethoxycarbonyl)-1-phenyl-ethyl]phenyl]-N'-(2,2-diethoxyethyl)-N'-(3-trifluoroacetyl-2,3,4,5-tetrahydro-1H-3-benzazepin-7-yl)-urea The [4-[2-(ethoxycarbonyl)-1-phenyl-ethyl]phenyl]isocyanate used is obtained from the corresponding amine by reacting with phosgene.

The crude product is used directly to prepared the compound of Example 5(6).
(12) 1-Formyl-4-(3-trifluoroacetyl-2,3,4,5-tetrahydro-1H-3-benzazepin-7-yl)-semicarbazide R$_f$ value: 0.41 (silica gel; methylene chloride/methanol= 9:1)

EXAMPLE IV 3-(tert.Butyloxycarbonyl)-7-[(2-hydroxyethyl)amino]-2,3,4,5-tetrahydro-1H-3-benzazepine 7.2 g of 7-amino-3-(tert.butyloxycarbonyl)-2,3,4,5-tetrahydro-1H-3-benzazepine (prepared from 7-nitro-2,3,4,5-tetrahydro-1H-3-benzazepine by reacting with di-tert.butyl pyrocarbonate and subsequent hydrogenation in the presence of palladium on activated charcoal) in 130 ml of methanol is mixed with 1.53 ml of glacial acetic acid and 1.8 g of glycolaldehyde (dimer) with stirring. Then 1.9 g of sodium cyanoborohydride are added and the mixture is stirred for one hour at ambient temperature. The reaction mixture is evaporated down and the residue is divided between ethyl acetate and water. The organic phase is separated off, washed twice with water, dried and evaporated down. The residue is purified by chromatography over a silica gel column with cyclohexane/ethyl acetate (4:6).

Yield: 5.4 g (64% of theory),

Melting point: 86°–89° C.,

R$_f$ value: 0.39 (silica gel; cyclohexane/ethyl acetate=4:6)

The following compound is obtained analogously to Example IV:
(1) methyl trans-4-[(2-hydroxyethyl)amino]-cinnamate Melting point: 117°–118° C.

R$_f$ value: 0.25 (silica gel; cyclohexane/ethyl acetate=1:1)

EXAMPLE V (4aRS,6RS,8aRS)-6-[(2,2-Dimethoxyethyl)amino]-2-methyl-1,2,3,4,4a,5,6,7,8,8a-decahydroisoquinoline To a solution of 9.0 g of (4aRS,8aRS)-2-methyl-6-oxo-1,2,3,4,4a,5,6,7,8,8a-decahydroisoquinoline and 6.8 g of aminoacetaldehyde-dimethylacetal in 90 ml of acetonitrile are added 31 ml of 3N hydrochloric acid and the mixture is stirred for 30 minutes at ambient temperature. Then it is cooled in an ice bath and 4.4 g of sodium cyanoborohydride are added in batches. After 30 minutes stirring at ambient temperature and standing overnight, the mixture is evaporated down, diluted with ice water and adjusted to a pH of 10–11. The mixture is extracted three times with ethyl acetate. The combined ethyl acetate extracts are washed twice with saturated saline solution, dried and evaporated down. The residue is purified by chromatography over an aluminium oxide column (basic).

Yield: 7.35 g (53% of theory),

R$_f$ value: 0.25 (aluminium oxide; ethyl acetate)
(1) (4aRS, 6SR, 8aRS)-6-[(2,2-dimethoxyethyl)amino]-2-methyl-1,2,3,4,4a,5,6,7,8,8a-decahydroisoquinoline is isolated as a by-product of Example V.

R$_f$ value: 0.56 (aluminium oxide; ethyl acetate)

EXAMPLE VI

7-Iodo-3-trifluoroacetyl-2,3,4,5-tetrahydro-1H-3-benzazepine 2.6 g of 7-amino-3-trifluoroacetyl-2,3,4,5-tetrahydro-1H-3-benzazepine are heated briefly with 50 ml of 10% hydrochloric acid with stirring, then cooled to 0° C. and 695 mg of sodium nitrite in 14 ml of water are added dropwise thereto at 0° C. with further cooling. A solution of 1.7 g of potassium iodide and 1.3 g of iodine in 10 ml of water is the added dropwise at 0° C. and the mixture is stirred overnight at ambient temperature. It is then decanted off and the residue obtained is dissolved in methylene chloride. The organic phase is washed with sodium disulphite solution and water, separated off, dried, filtered and evaporated down.

The crude product is purified by chromatography over a silica gel column with cyclohexane/ethyl acetate (4:1).

Yield: 2.4 g (65% of theory),
Melting point: 80°–82° C.
$R_f$ value: 0.61 (silica gel; cyclohexane/ethyl acetate=4:1)

EXAMPLE VII

7-Amino-3-trifluoroacetyl-2,3,4,5-tetrahydro-1H-3-benzazepine 3 g of 7-nitro-3-trifluoroacetyl-2,3,4,5-tetrahydro-1H-3-benzazepine are hydrogenated in 200 ml of ethyl acetate with 3 g of 10% palladium on activated charcoal at ambient temperature under a hydrogen pressure of 50 psi for one hour. The catalyst is removed by suction filtration and the filtrate is evaporated down. The residue is heated with tert.butylmethylether and then cooled. The precipitate is suction filtered, washed with tert.butylmethylether and dried.

Yield: 12.2 g (79% of theory),
Melting point: 102°–104° C.
$R_f$ value: 0.31 (silica gel; cyclohexane/ethyl acetate=2:1)

The following compounds are obtained analogously to Example VII:
(1) 7-amino-3-tert.butyloxycarbonyl-2,3,4,5-tetrahydro-1H-3-benzazepine The 3-tert.butyloxycarbonyl-7-nitro-2,3,4,5-tetrahydro-1H-3-benzazepine used as starting material (Melting point: 100°–102° C.) is obtained by reacting 7-nitro-2,3,4,5-tetrahydro-1H-3-benzazepine-hydrochloride with di-tert.butyl pyrocarbonate in the presence of sodium hydroxide solution.

$R_f$ value: 0.40 (silica gel; cyclohexane/ethyl acetate=7:3)
(2) 7-amino-3-ethyl-2,3,4,5-tetrahydro-1H-3-benzazepine Carried out with Raney nickel in methanol.

$R_f$ value: 0.58 (silica gel; toluene/dioxane/methanol/conc. aqueous ammonia=20:50:20:3)
(3) ethyl 3-(4-aminophenyl)-3-phenyl-propionatehydrochloride Carried out in ethanol in the presence of ethanolic hydrochloric acid. The starting material ethyl 3-(4-nitrophenyl)-3-phenylacrylate [$R_f$ value: 0.36 (silica gel; cyclohexane/methylene chloride=1:1)] is obtained by reacting 4-nitrobenzophenone with triethyl phosphonoacetic acid.

$R_f$ value: 0.40 (Reversed Phase silica gel; methanol/5% aqueous saline solution=6:4)

EXAMPLE VIII

7-Nitro-3-trifluoroacetyl-2,3,4,5-tetrahydro-1H-3-benzazepine

To a solution of 23.3 g of 3-trifluoroacetyl-2,3,4,5-tetrahydro-1H-3-benzazepine [$R_f$ value: 0.76 (silica gel; cyclohexane/ethyl acetate=1:1), prepared by reacting 2,3,4,5-tetrahydro-1H-3-benzazepine with trifluoroacetic acid anhydride in the presence of N-ethyl-diisopropylamine] in 60 ml of conc. sulphuric acid is added dropwise within 1.5 hours, at 0° to 8° C., a mixture of 9.7 g of potassium nitrate and 50 ml of conc. sulphuric acid. The mixture is heated to ambient temperature, poured on to 1 liter of ice and extracted with ethyl acetate. The combined ethyl acetate phases are washed with water and with saturated saline solution, dried and evaporated down. The residue is heated with tert.butyl-methylether. It is then cooled, and the product is suction filtered and washed with tert.butyl-methylether.

Yield: 16.2 g (59% of theory),
Melting point: 116°–119° C.
$R_f$ value: 0.57 (silica gel; cyclohexane/ethyl acetate=2:1)

The following compound is obtained analogously to Example VIII:
(1) 7-nitro-2,3,4,5-tetrahydro-1H-3-benzazepine-hydrochloride Carried out with sulphuric acid/potassium nitrate and isolated as the hydrochloride Melting point: 235°–238° C. (Decomp.)
Calc.: C 52.52 H 5.74 N 12.25 Cl 15.50 Found: 52.44 5.80 12.07 15.36

EXAMPLE IX

4-[4-[2-(Methoxycarbonyl)ethyl]phenyl]-5-methyl-4H-1,2,4-triazol-3-one 8.1 g of 1-acetyl-4-[4-[2-(methoxycarbonyl)ethyl]phenyl]-semicarbazide are heated with 60 ml of 1N sodium hydroxide solution over a steam bath for 1.5 hours. The mixture is then cooled somewhat, filtered and the filtrate is acidified slightly with citric acid. It is filtered and the filtrate is combined with concentrated hydrochloric acid. The precipitate is filtered, washed with water and dried. The intermediate product is stirred overnight in methanol with some methanolic hydrochloric acid. The reaction mixture is evaporated down and the residue is triturated with tert.butylmethylether, suction filtered and dried.

Yield: 4.98 g (65% of theory),
$R_f$ value: 0.40 (silica gel; toluene/dioxane/ethanol/glacial acetic acid=90:10:10:6)
Calc.: C 59.76 H 5.79 N 16.08 Found: 59.54 5.86 16.05

The following compounds are obtained analogously to Example IX:
(1) 4-[trans-4-[2-(methoxycarbonyl)ethyl]cyclohexyl]-5-methyl-4H-1,2,4-triazol-3-one Melting point: 179°–181° C.
(2) 4-[trans-4-[2-(methoxycarbonyl)ethyl]cyclohexyl]-4H-1,2,4-triazol-3-one Melting point: 142°–144° C.
(3) 4-(3-tert.butyloxycarbonyl-2,3,4,5-tetrahydro-1H-3-benzazepin-7-yl)-4H-1,2,4-triazol-3-one starting material: compound of example III (12)

The intermediate product is reacted with di-tert.butylpyrocarbonate instead of methanolic hydrochloric acid.

melting point: 185°–186° C.
$R_f$ value: 0.25 (silica gel; cyclohexane/ethyl acetate=2:3)

EXAMPLE X

N-[trans-4-[2-(Methoxycarbonyl)ethyl]cyclohexyl]ethanolamine 5.0 g of N-benzyl-N-[trans-4-[2-(methoxycarbonyl)ethyl]cyclohexyl]-ethanolamine are hydrogenated in 150 ml of methanol with 1.0 g of 10% palladium on activated charcoal for 1 ¾ hours at 50° C. under a hydrogen pressure of 50 psi. The mixture is filtered and evaporated down.

Yield: 3.3 g (92% of theory),
$R_f$ value: 0.20 (silica gel; methylene chloride/methanol/conc. aqueous ammonia=9:1:0.4)

The following compounds are obtained analogously to Example X:
(1) tert.butyl (trans-4-aminocyclohexyl)oxyacetate The starting material, tert.butyl [trans-(4dibenzylamino)cyclohexyl]-oxyacetate [
$R_f$ value: 0.51; (silica gel; cyclohexane/ethyl acetate= 4:1)], is obtained by reacting trans-4-(dibenzylamino)cyclohexanol with tert.butyl bromoacetate in toluene/50% sodium hydroxide solution in the presence of tetrabutylammonium-hydrogen sulphate.

$R_f$ value: 0.56 (Reversed Phase silica gel; methanol/5% aqueous saline solution=6:4).

(2) N-(3-hydroxypropyl)-N-[trans-4-[2-(methoxycarbonyl)ethyl]cyclohexyl]-amine $R_f$ value: 0.10 (silica gel; methylene chloride/methanol= 9:1)

(3) methyl [[trans-4-[2-(methoxycarbonyl)ethyl]cyclohexyl]amino]-acetate-hydrochloride Melting point: 166°–168° C.

Hydrogenation in the presence of methanolic hydrochloric acid.

$R_f$ value: 0.69 (silica gel; methylene chloride/methanol/conc. aqueous ammonia=95:5:1)

EXAMPLE XI

N-Benzyl-N-[trans-4-[2-(methoxycarbonyl)ethyl]cyclohexyl]-ethanolamine 6.2 g of N-[trans-4-[2-(methoxycarbonyl)ethyl]cyclohexyl]-benzylamine-hydrochloride, 12.8 g of N-ethyl-diisopropylamine and 5.0 g of 2-bromoethanol are stirred at 100° C. for 22 hours and then cooled. The mixture is divided between ethyl acetate and water, the aqueous phase is extracted with ethyl acetate and the combined ethyl acetate phases are washed with saturated saline solution. The ethyl acetate phase is evaporated down and the residue is purified by chromatography over a silica gel column using methylene chloride/methanol (9:1).

Yield: 5.1 g (80% of theory), $R_f$ value: 0.67 (silica gel; methylene chloride/methanol= 9:1)

The following compounds are obtained analogously to Example XI:

(1) N-(3-hydroxypropyl)-N-[trans-4-[2-(methoxycarbonyl)ethyl]cyclohexyl]-benzylamine $R_f$ value: 0.70 (silica gel; methylene chloride/methanol =9:1).

(2) methyl N-benzyl-[[trans-4-[(2 -methoxycarbonyl)ethyl]cyclohexy]amino]-acetate $R_f$ value: 0.86 (silica gel; cyclohexane/ethyl acetate=3:7)

(3) 3-ethyl-7-nitro-2,3,4,5-tetrahydro-1H-3-benzazepine $R_f$ value: 0.32 (silica gel; methylene chloride/methanol =95:5)

EXAMPLE XII

N-[trans-4-[2-(Methoxycarbonyl)ethyl]cyclohexyl]benzylamine-hydrochloride 8.0 g of methyl 3-(trans-4-aminocyclohexyl)propionate-hydrochloride, 4.3 g of benzaldehyde and 5.0 ml of triethylamine in 150 ml of methanol are hydrogenated with 1.0 g of Raney nickel at 50° C. under a hydrogen pressure of 50 psi for 4 hours. After cooling, the mixture is suction filtered and the filtrate is evaporated down. The residue is divided between ethyl acetate and water, the aqueous phase is adjusted to pH 8–9 with sodium hydroxide solution and extracted with ethyl acetate. The combined ethyl acetate phases are washed with saturated saline solution, dried and evaporated down. The residue is suspended in diethylether and mixed with methanolic hydrochloric acid. The precipitate is suction filtered, washed with diethylether and dried.

Yield: 7.4 g (66% of theory),

Melting point: 170°–172° C.

Calc.: C 65.47 H 8.40 N 4.49 Cl 11.37 Found: 65.38 8.44 4.46 11.40

EXAMPLE XIII

Methyl (trans-4-aminocyclohexyl)oxyacetate-hydrochloride

Hydrochloric acid gas is piped for an hour over a solution of 59.4 g of tert.butyl (trans-4-aminocyclohexyl)oxyacetate in 500 ml of methanol, cooled in an ice bath, and then the mixture is stirred overnight at ambient temperature. It is evaporated to dryness, the residue is triturated with acetone and the solid is suction filtered and dried.

Yield: 34.3 g (59% of theory),

Melting point: 157°–160° C.

EXAMPLE XIV 2-(3-Trifluoroacetyl-2,3,4,5-tetrahydro-1H-3-benzazepin-7-yl)-3,4-dihydro-2H,5H-1,2,5-thiadiazole-1,1-dioxide a) N-(2-Chloroethyl)-N'-(3-trifluoroacetyl-2,3,4,5-tetrahydro-1H-3-benzazepin-7-yl)-sulphuric acid diamide To a mixture of 7.6 g of 7-amino-3-trifluoroacetyl-2,3,4,5-tetrahydro-1H-3-benzazepine and 7.7 ml of N-ethyl-diisopropylamine in 70 ml of methylene chloride are added dropwise, at −5° C., 4.8 g of [(2-chloroethyl)amino] sulphonylchloride in 30 ml of methylene chloride. The mixture is stirred for an hour at 0° C. and overnight at ambient temperature. The reaction mixture is diluted with methylene chloride and washed with water, 1N hydrochloric acid and again with water. The organic phase is dried, evaporated down and the residue is purified by chromatography over a silica gel column using cyclohexane/ethyl acetate (1:1).

Yield: 7.8 g (72% of theory),

Melting point: 128°–130° C.

$R_f$ value: 0.64 (silica gel; cyclohexane/ethyl acetate=1:1)

b) 2-(3-Trifluoroacetyl-2,3,4,5-tetrahydro-1H-3-benzazepin-7-yl)-3,4-dihydro-2H,5H-1,2,5-thiadiazole-1,1-dioxide 7.8 g of the compound of Example XIVa) are dissolved in 20 ml of dimethylformamide and mixed with 2.5 g of potassium tert.butoxide. After 3 hours stirring at ambient temperature, it is added to 300 ml of an aqueous 15% citric acid solution and extracted three times with ethyl acetate. The combined organic phases are dried and evaporated down and the residue is purified by chromatography over a silica gel column using cyclohexane/ethyl acetate (1:1).

Yield: 2.1 g (30% of theory)

Melting point: 165°–167° C.

$R_f$ value: 0.30 (silica gel; cyclohexane/ethyl acetate=1:1)

EXAMPLE XV (3-Methyl-2,3,4,5-tetrahydro-1H-3-benzazepin-7-yl)-boric acid

To 7.1 g 7-jodo-3-methyl-2,3,4,5-tetrahydro-1H-3-benzazepin ($R_f$ value: 0.85 (silica gel; toluene/dioxane/methanol/conc. aqueous ammonia=20:50:20:5); prepared from the compound of example VI by reaction with sodium hydroxide solution/methanol and subsequent reaction with formaline/formic acid]in 50 ml of diethylether are given at −70° to −75° C. 17.7 ml of 1.6 M n-butyl lithium, dissolved in hexane. After stirring for 30 minutes at −70° C. 5.7 ml of triisopropyl borate in 30 ml of diethylether are added to the reaction mixture. Subsequently the mixture is stirred one hour at −75° C., then warmed up to −50° C. After adding 70 ml of water and stirring for one hour at room temperature, the aqueous phase was separated. The aqueous phase is adjusted to a pH-value of 8 to 8.5 with glacial acetic acid. The precipitate is filtered, washed with a small amount of cold water and dried at 60° C.

Yield: 3.7 g (73% of theory),
melting point: 153°–155° C. (sintering from 148° C.)
$R_f$ value: 0.80 (reversed phase silica gel; methanol/5% aqueous saline solution=6:4)

EXAMPLE XVI

1-[2-(ethoxycarbonyl)ethyl]-3-[4-(trifluoromethylsulfonyloxy)phenyl]-imidazolidin-2-one a) N-(2,2-Diethoxyethyl)-4-benzyloxy-aniline Prepared from 4-benzyloxy-aniline and bromoacetaldehy-dediethylacetal in the presence of N-ethyl-diisopropylamine.

$R_f$ value: 0.42 (silica gel; cyclohexane/ethyl acetate=85:15)

b) N-(4-Benzyloxyphenyl)-N-(2,2-diethoxyethyl)-N'-[2-(ethoxycarbonyl)ethyl]-urea Prepared from N-(2,2-diethoxyethyl)-4-benzyloxyaniline and [2-(ethoxycarbonyl)ethyl]-isocyanate.

$R_f$ value: 0.45 (silica gel;cyclohexane/ethyl acetate=1:1 c) 1-(4-Benzyloxyphenyl)-3-[2-(ethoxycarbonyl)ethyl] 3H-imidazol-2-one

Prepared from N-(4-benzyloxyphenyl)-N-(2,2-diethoxyethyl)-N'-[2-(ethoxycarbonyl)ethyl]-urea and trifluoroacetic acid in methylene chloride.

melting point: 66°–68° C.

$R_f$ value: 0.41 (silica gel; cyclohexane/ethyl acetate=1:1)

d) 1-(4-hydroxyphenyl)-3-[2-(ethoxycarbonyl)ethyl]imidazolidin-2-one

Prepared from 1-(4-benzyloxyphenyl)-3-[2-(ethoxycarbonyl)ethyl]-3H-imidazol-2-one by hydrogenation in the presence of palladium on charcoal in ethanol at 40° C. and a hydrogen pressure of 50 psi.

$R_f$ value: 0.20 (silica gel; methylene chloride/methanol= 100:2)

e) 1-[2-(Ethoxycarbonyl)ethyl]-3-[4-(trifluoromethylsulfonyloxy)-phenyl]-imidazolidin-2-on Prepared from 1-(4-hydroxyphenyl)-3-[2-(ethoxycarbonyl)ethyl]-imidazolidin-2-one and trifluoromethanesulfonic acid anhydride in pyridine at 0° C.

melting point: 81°–83° C.

$R_f$ value: 0.66 (silica gel; methylene chloride/methanol= 100:1)

Calculated: C 43.90 H 4.18 N 6.83 S 7.81 Found: 43.92 4.20 6.98 7.91

EXAMPLE 1

1-(1-Aminoisoquinolin-6-yl)-3-[4-(2-carboxyethyl)phenyl]-imidazolidin-2-one×1 water×1.2 acetic acid 300 mg of 3-[4-(2-carboxyethyl)phenyl]-1-(1-chloroisoquinolin-6-yl)-imidazolidin-2-one, 895 mg of acetamide and 524 mg of potassium carbonate are mixed thoroughly in a mortar and then heated to 200° C. for 3 hours under nitrogen and with stirring. After cooling the mixture is combined with 20 ml of water and adjusted to pH 8–9 using 1N hydrochloric acid. The precipitate is suction filtered and washed several times with water. After drying, the precipitate is suspended in 50 ml of methylene chloride/methanol (4:1) and exposed to ultrasound for 30 minutes in an ultrasound bath. The precipitate is suction filtered and the treatment with methylene chloride/methanol in the ultrasound bath is repeated twice. The filter residue is stirred in a mixture of 30 ml of methanol and 10 ml of glacial acetic acid with gentle heating. The insoluble matter is filtered off and the mother liquor is evaporated to dryness. The residue is mixed with toluene once again and evaporated down. Then it is dried at 60° C. in vacuo.

Yield: 70 mg (20% of theory),
Melting point: >250° C.,
$R_f$ value: 0.78 (Reversed Phase silica gel; methanol/5% aqueous saline solution=8:4)
Calc.: C 60.25 H 5.79 N 12.01 Found: 60.20 5.43 11.54
Mass spectrum: M$^+$=376

EXAMPLE 2

3-[4-(2-Carboxyethyl)phenyl]-1-(1-chloroisoquinolin-6-yl)-imidazolidin-2-one 1 g of 1-(1-chloroisoquinolin-6-yl)-3-[4-[2-(methoxycarbonyl)-ethyl]phenyl]-imidazolidin-2-one, 100 ml of dioxane, 80 ml of water and 8.5 ml of 1N sodium hydroxide solution are stirred for 3 hours at ambient temperature. 9 ml of 1N hydrochloric acid are added, the mixture is evaporated down and the precipitate is suction filtered. The product is washed with water and dried at 50° C.

Yield: 0.78 g (80% of theory),

Melting point: 236°–240° C. (Decomp.)

$R_f$ value: 0.36 (silica gel; methylene chloride/ethanol/ ethyl acetate=20:1:1)

The following compounds are obtained analogously to Example 2:

(1) 1-[4-(2-carboxyethyl)phenyl]-3-(isoquinolin-6-yl)-3H-imidazol-2-one

Melting point: 305°–310° C., $R_f$ value: 0.49 (silica gel; methylene chloride/methanol =9:1)

Calc.: C 70.18 H 4.77 N 11.69 Found: 69.95 4.93 11.64

(2) 1-[4-(2-carboxyethyl)phenyl]-3-(1,2,3,4-tetrahydroisoquinolin-6-yl)-imidazolidin-2-one $R_f$ value: 0.44 (Reversed Phase silica gel; methanol/5% aqueous saline solution=6:4)

Calc.: C 67.54 H 6.21 N 11.25 Found: 67.58 6.42 11.23

(3) 1-[4 -(2-carboxyethyl)phenyl]-3-(2,3,4,5-tetrahydro-1H-3 -benzazepin-7-yl)-3H-imidazol-2-one (4) 2-[trans-4-(2-methoxycarbonyl)ethyl]-5-(2,3,4,5-tetrahydro-1H-3-benzazepin-7-yl)-3,4-dihydro-2H,5H-1,2,5-thiadiazole-1,1-dioxide Carried out in methanol/sodium hydroxide solution; starting material: compound of Example 18.

$R_f$ value: 0.36 (Reversed Phase silica gel; methanol/5% aqueous saline solution=6:4)

(5) 3-[4-(2-carboxyethyl)phenyl]-1-(2,3,4,5-tetrahydro-1H-3-benzazepin-7-yl)-imidazolidin-2,4-dione (6) 1-[4-[2-carboxy-2-(n-butylsulphonylamino)ethyl] phenyl]-3-(2,3,4,5-tetrahydro-1H-3-benzazepin-7-yl)-imidazolidin-2-one (7) 1-[4-[2-carboxy-2-(n-pentylcarbonylamino)ethyl] phenyl]-3-(2,3,4,5-tetrahydro-1H-3-benzazepin-7-yl)-imidazolidin-2-one (8) 1-[4-(2-carboxyethyl)phenyl]-3-(5,6,7,8-tetrahydropyrido[3,4-d]pyrimidin-2-yl)-imidazolidin-2-one (9) 1-[4-[(carboxymethyl)sulphonyl]phenyl]-3-(2,3,4,5-tetrahydro-1H-3-benzazepin-7-yl)-imidazolidin-2-one

(10) 1-[(4-carboxy-1-piperidinyl)carbonylmethyl]-3-(2,3, 4,5-tetrahydro-1H-3-benzazepin-7-yl)-imidazolidin-2-one

(11) 1-[2-[(2-carboxyethyl)aminocarbonyl]ethyl]-3-(2,3, 4,5-tetrahydro-1H-3-benzazepin-7-yl)-imidazolidin-2-one

(12) 1-[4-(2-carboxyethyl)phenyl]-3-(2,3,4,5-tetrahydro-1H-2-benzazepin-7-yl)-imidazolidin-2-one

(13) 1-[4-(2-carboxyethyl)phenyl]-3-(1,1-dimethyl-1,2,3, 4-tetrahydro-isoquinolin-6-yl)-imidazolidin-2-one

EXAMPLE 3

1-(1-Chloroisoquinolin-6-yl)-3-[4-[2-(methoxycarbonyl)-ethyl]-phenyl]-imidazolidin-2-one 2.2 g of 1-(isoquinolin-N-oxid-6-yl)-3-[4-[2-(methoxycarbonyl)-ethyl]phenyl]-imidazolidin-2-one and 25 ml of phosphorus oxychloride are refluxed for 2 hours. The phosphorus oxychloride is then distilled off and the residue is mixed with ice. The pH of the mixture is adjusted to 8–9 using saturated sodium hydrogen carbonate solution. It is extracted several times with methylene chloride, the organic phases are dried and evaporated down and the residue is purified by chromatography over a silica gel column with methylene chloride/methanol (20:1).

Yield: 1.0 g (43% of theory),
$R_f$ value: 0.66 (silica gel; methylene chloride/methanol=20:1)

EXAMPLE 4

1-(Isoquinolin-6-yl)-3-[4-[2-(methoxycarbonyl)ethyl]phenyl]-imidazolidin-2-one

To a solution of 3.0 g of N-(2-hydroxyethyl)-N'-(isoquinolin-6-yl)-N-[4-[2-(methoxycarbonyl)ethyl]phenyl]-urea and 2.0 g of triphenylphosphine in 105 ml of acetonitrile are added, at an internal temperature of 42° to 52° C., 1.31 ml of diethyl azodicarboxylate in 36 ml of acetonitrile. After 2 hours stirring at 45° C. the mixture is cooled to −5° C. and stirred for a further 2 hours. The precipitate is suction filtered and washed with a little cold acetonitrile.

Yield: 2.6 g (90% of theory),
Melting point: 213°–215° C.,
$R_f$ value: 0.60 (silica gel; methylene chloride/methanol =20:1:1)

The following compounds are obtained analogously to Example 4:

(1) 1-(3-tert.butyloxycarbonyl-2,3,4,5-tetrahydro-1H-3-benzazepin-7-yl)-3-[4-[2-(methoxycarbonyl)ethyl]phenyl] imidazolidin-2-one Melting point: 165°–167° C.
$R_f$ value: 0.77 (silica gel; methylene chloride/ethyl acetate=9:1)

(2) 1-[trans-4-[2-(methoxycarbonyl)ethyl]cyclohexyl]-3-(3-trifluoroacetyl-2,3,4,5-tetrahydro-1H-3-benzazepin-7-yl)-imidazolidin-2-one Melting point: 250°–255° C. (Decomp.)
$R_f$ value: 0.45 (silica gel; cyclohexane/ethyl acetate=1:1)

(3) 1-[4-[trans-2-(methoxycarbonyl)ethenyl]phenyl]-3-(3-trifluoroacetyl-2,3,4,5-tetrahydro-1H-3-benzazepin-7-yl)-imidazolidin-2-one Melting point: 216°–220° C.
$R_f$ value: 0.38 (silica gel; cyclohexane/ethyl acetate=1:1)

(4) 1-[trans-4-[2-(methoxycarbonyl)ethyl]cyclohexyl]-3-(3-trifluoroacetyl-2,3,4,5-tetrahydro-1H-3-benzazepin-7-yl)-3,4,5,6-tetrahydro-1H-pyrimidin-2-one Melting point: 125°–127° C.
$R_f$ value: 0.54 (silica gel; cyclohexane/ethyl acetate=1:2)

EXAMPLE 5

1-(Isoquinolin-6-yl)-3-[4-[2-(methoxycarbonyl)ethyl]phenyl]-3H-imidazol-2-one 7.3 g of N-(2,2-diethoxyethyl)-N'-(isoquinolin-6-yl)-N-[4-[2-(methoxycarbonyl)ethyl]phenyl]-urea are stirred in 35 ml of trifluoroacetic acid for 2 hours at ambient temperature. Then the mixture is partly evaporated down and ice water is added. It is made alkaline with sodium hydroxide solution, with stirring and cooling, the precipitate is suction filtered and washed with a little methanol. The product is then recrystallised from methanol.

Yield: 4.45 g (76% of theory),
Melting point: 158°–161° C.,
$R_f$ value: 0.29 (silica gel; methylene chloride/methanol =95:5)
Calc.: C 70.76 H 5.13 N 11.25 Found: 70.52 5.08 11.35

The following compounds are obtained analogously to Example 5:

(1) 1-[trans-4-[2-(methoxycarbonyl)ethyl]cyclohexyl]-3-(3-trifluoroacetyl-2,3,4,5-tetrahydro-1H-3-benzazepin-7-yl)-3H-imidazol-2-one Carried out by dry heating to 160°–170° C.
Melting point: 121°–124° C.,
$R_f$ value: 0.35 (silica gel; cyclohexane/ethyl acetate=1:1).

(2) 1-[trans-4-[[(methoxycarbonyl)methyl]oxy]-cyclohexyl]-3-(3-trifluoroacetyl-2,3,4,5-tetrahydro-1H-3-benzazepin-7-yl)-3H-imidazol-2-one Melting point: 148°–149° C.
$R_f$ value: 0.28 (silica gel; ethyl acetate/cyclohexane=2:1)

(3) 1-[4-[2-(ethoxycarbonyl)-1-propyl]phenyl]-3-(3-trifluoroacetyl-2,3,4,5-tetrahydro-1H-3-benzazepin-7-yl)-3H-imidazol-2-one $R_f$ value: 0.32 (silica gel; cyclohexane/ethyl acetate=2:1)

(4) 1-[trans-4-[2-(methoxycarbonyl)ethyl]cyclohexyl]-3-(3-ethyl-2,3,4,5-tetrahydro-1H-3-benzazepin-7-yl)-3H-imidazol-2-one $R_f$ value: 0.30 (Reversed Phase silica gel; methanol/5% aqueous saline solution=6:4)

(5) 1-[trans-4-[2-(methoxycarbonyl)ethyl]cyclohexyl]-3-(7-ethyl-6,7,8,9-tetrahydro-5H-pyrazino[2,3-d]azepin-2-yl)-3H-imidazol-2-one Melting point: 135°–136° C. Calc.: C 64.61 H 7.78 N 16.38 Found: 64.82 7.84 16.27

(6) 1-[4-[29-(ethoxycarbonyl)-1-phenyl-ethyl]phenyl]-3-(3-trifluoroacetyl-2,3,4,5-tetrahydro-1H-3-benzazepin-7-yl)-3H-imidazol-2-one $R_f$ value: 0.24 (silica gel; cyclohexane/ethyl acetate=7:3)

(7) 1-[trans-4-[2-(methoxycarbonyl) ethyl]cyclohexyl]-3-(7-benzyl-6,7,8,9-tetrahydro-5H-pyrimido[4,5-d]azepin-2-yl)-3H-imidazol-2-one Melting point: 131°–134° C.
$R_f$ value: 0.38 (silica gel; methylene chloride/methanol =20:1)

1-[4-[2-(Methoxycarbonyl)ethyl]phenyl]-3-(1,2,3,4-tetrahydro-isoquinolin-6-yl)-imidazolidin-2-one-acetate 2.0 g of 1-(isoquinolin-6-yl)-3-[4-[2-(methoxycarbonyl)-ethyl]-phenyl]-3H-imidazol-2-one in 50 ml of glacial acetic acid are hydrogenated with 0.5 g of platinum oxide at ambient temperature under a hydrogen pressure of 50 psi for 40 minutes. The catalyst is filtered off, the filtrate is evaporated down and the residue is recrystallized from methanol.

Yield: 1.7 g (72% of theory),
Melting point: 170°–173° C. (Decomp.)
Calc.: C 65.59 H 6.65 N 9.56 Found: 65.90 6.78 9.69
$R_f$ value: 0.30 (silica gel; toluene/dioxane/methanol/conc. aqueous ammonia =20:50:20:5)
Mass spectrum: $M^+$=379

The following compounds are obtained analogously to Example 6:

(1) 1-[trans-4-[2-(methoxycarbonyl)ethyl]cyclohexyl]-3-(1,2,3,4-tetrahydro-isoquinolin-6-yl)-imidazolidin-2-one-acetate (2) 1-[trans-4-(2-Carboxyethyl)cyclohexyl]-3-(3-methyl-2,3,4,5,5a,6,7,8,9,9a-decahydro-1H-3-benzazepin-7-yl)imidazolidin-2-one×1.35 HCl×1.9 $H_2O$ Dioxane/water and platinum-rhodium-catalyst are used.

As starting material is used the compound of example 19.
Mass spectrum: M$^+$=405
Calculated: C 56.49 H 9.10 N 8.5 Cl 9.79 56.63 8.81 8.60 9.92

(3) 1-[trans-4-(2-Carboxyethyl)cyclohexyl]-3-(2,3,4,5,5a,6,7,8,9,9a-decahydro-1H-3-benzazepin-7-yl)imidazolidin-2-one-×1.05 HCl×0.9 H$_2$O Dioxane/water and platinium-rhodium-catalyst are used. As starting material is use the compound of example 14(1)
Mass spectrum: M$^+$=391
Calculated: C 59.43 H 9.03 N 9.45 Cl 8.05 59.49 8.83 9.35 8.30

EXAMPLE 7

1-[4-[2-(Isobutyloxycarbonyl)ethyl]phenyl]-3-(1,2,3,4-tetrahydroisoquinolin-6-yl)-imidazolidin-2-one-hydrochloride ×1 water Hydrochloric acid is piped for 30 minutes, with stirring, over a suspension of 150 mg of 1-[4-(2-carboxyethyl)phenyl]-3-(1,2,3,4-tetrahydro-isoquinolin-6-yl)-imidazolidin-2-one in 4.6 ml of isobutanol. The mixture is stirred overnight at ambient temperature, acetone is added and the precipitate is suction filtered. The product is suspended in acetone, suction filtered, washed with acetone and diethylether and dried.

Yield: 140 mg (77% of theory),
Calc.: C 65.56 H 7.04 N 9.18 Cl 7.74 Found: 65.38 7.03 9.47 7.92
R$_f$ value: 0.19 (Reversed Phase silica gel; methanol/5% saline solution=6:4)
Mass spectrum: M$^+$=421

The following compounds are obtained analogously to Example 7:

(1) 1-[4-[2-(isopropyloxycarbonyl)ethyl]phenyl]-3-(2,3,4,5-tetrahydro-1H-3-benzazepin-7-yl)-imidazolidin-2-one-hydrochloride
Calc.: C 63.08 H 7.20 N 8.83 Cl 7.45 Found: 62.79 7.14 8.83 7.80
R$_f$ value: 0.21 (Reversed Phase silica gel; methanol/5% saline solution=6:4)
Mass spectrum: M$^+$=421

(2) 1-[4-[2-(cyclohexyloxycarbonyl)ethyl]phenyl]-3-(2,3,4,5-tetrahydro-1H-3-benzazepin-7-yl)-imidazolidin-2-one-hydrochloride (3) 1-[4-[2-(methoxycarbonyl)ethyl]phenyl]-3-(3-methyl-2,3,4,5-tetrahydro-1H-3-benzazepin-7-yl)-imidazolidin-2-one-hydrochloride×0.75 H$_2$O
Melting point: 248°–250° C.,
Calc.: C 63.01 H 6.94 N 9.19 Cl 7.75 Found: 63.09 6.98 9.22 7.88
R$_f$ value: 0.28 (Reversed Phase silica gel; methanol/5% aqueous saline solution=6:4)

(4) 1-[4-[2-(ethoxycarbonyl)ethyl]phenyl]-3-(3-methyl-2,3,4,5-tetrahydro-1H-3-benzazepin-7-yl)-imidazolidin-2-one-hydrochloride
R$_f$ value: 0.22 (Reversed Phase silica gel; methanol/5% aqueous saline solution=6:4)

(5) 1-[4-[2-(isopropyloxycarbonyl)ethyl]phenyl]-3-(3-methyl-2,3,4,5-tetrahydro-1H-3-benzazepin-7-yl)imidazolidin-2-one-hydrochloride
R$_f$ value: 0.19 (Reversed Phase silica gel; methanol/5% aqueous saline solution=6:4)

(6) 1-[trans-4-[2-(isopropyloxycarbonyl)ethyl]cyclohexyl]-3-(3-methyl-2,3,4,5-tetrahydro-1H-3-benzazepin-7-yl)-imidazolidin-2-one-hydrochloride Thionylchloride and hydrochloric acid gas are used.
Melting point: >250° C.,
R$_f$ value: 0.17 (Reversed Phase silica gel; methanol/5% aqueous saline solution=6:4)
Calc.: C 65.32 H 8.43 N 8.79 Cl 7.42 Found: 65.10 8.41 8.91 7.66

(7) 1-[trans-4-[2-(ethoxycarbonyl)ethyl]cyclohexyl]-3-(3-methyl-2,3,4,5-tetrahydro-1H-3-benzazepin-7-yl)imidazolidin-2-one-hydrochloride
Thionylchloride and hydrochloric acid gas are used.
Melting point: >250° C.,
R$_f$ value: 0.24 (Reversed Phase silica gel; methanol/5% aqueous saline solution=6:4)
Calc.: C 64. 71 H 8.25 N 9.09 Cl 7.64 Found: 64. 09 8.22 9.08 7.72

(8) 1-[trans-4-[2-(methoxycarbonyl)ethyl]cyclohexyl]-3-(3-methyl-2,3,4,5-tetrahydro-1H-3-benzazepin-7-yl)imidazolidin-2-one-hydrochloride
Thionylchloride and hydrochloric acid gas are used.
Melting point: >250° C.,
R$_f$ value: 0.29 (Reversed Phase silica gel; methanol/5% aqueous saline solution=6:4)
Calc.: 64.05 H 8.04 N 9.34 Cl 7.88 Found: 64.10 7.97 9.52 8.11

(9) 1-[trans-4-[2-(isopropyloxycarbonyl)ethyl]cyclohexyl]-3-(2,3,4,5-tetrahydro-1H-3-benzazepin-7-yl)imidazolidin-2-one-hydrochloride
Thionylchloride and hydrochloric acid gas are used.
R$_f$ value: 0.20 (Reversed Phase silica gel; methanol/5% aqueous saline solution=6:4)

(10) 1-[trans-4-[2-(ethoxycarbonyl)ethyl]cyclohexyl]-3-(2,3,4,5-tetrahydro-1H-3-benzazepin-7-yl)-imidazolidin-2-one-hydrochloride
Thionylchloride and hydrochloric acid gas are used. R$_f$ value: 0.23 (Reversed Phase silica gel; methanol/5% aqueous saline solution=6:4)
Calc.: C 64.05 H 8.06 N 9.34 Cl 7.88 Found: 63.77 8.23 9.07 7.91

(11) 1-[trans-4-[2-(methoxycarbonyl)ethyl]cyclohexyl]-3-(2,3,4,5-tetrahydro-1H-3-benzazepin-7-yl)-imidazolidin-2-one-hydrochloride
Thionylchloride and hydrochloric acid gas are used.
R$_f$ value: 0.26 (Reversed Phase silica gel; methanol/5% aqueous saline solution=6:4)
Calc.: C 63.36 H 7.86 N 9.64 Cl 8.13 Found: 63.34 7.88 9.73 8.11

EXAMPLE 8

1-[4-(2-Carboxyethyl)phenyl]-3-(2-methyl-1,2,3,4-tetrahydroisoquinolin-6-yl)-imidazolidin-2-one×0.2 water 350 mg of 1-[4-[2-(methoxycarbonyl)ethyl]phenyl]-3-(1,2,3,4-tetrahydroisoquinolin-6-yl)-imidazolidin-2-one acetate, 0.7 ml of water, 0.15 ml of formic acid and 0.7 ml of 37% aqueous formaldehyde solution are stirred for one hour at 65° C. Toluene is added and the mixture is evaporated down. It is mixed with toluene and evaporated down once more. The residue is stirred with 2 ml of tetrahydrofuran, 1 ml of water and 0.8 ml of 4N sodium hydroxide solution for 2 ½ days at ambient temperature. 220 mg of ammonium chloride in 1 ml of water are added and the mixture is stirred for 2 hours. The reaction mixture is partly evaporated down, cooled with ice and the solid product is suction filtered. The solid is washed with water, acetone and diethylether and then dried.

Yield: 220 ml (72% of theory),
Melting point: 245°–248° C.,
Calc.: C 68.98 H 6.68 N 10.97 Found: 68.91 6.69 10.92

R_f value: 0.41 (Reversed Phase silica gel; methanol/5% aqueous saline solution=6:4)

Mass spectrum: M$^+$=379

The following compound is obtained analogously to Example 8:

(1) 1-[4-(2-carboxyethyl)phenyl]-3-(3-methyl-2,3,4,5-tetrahydro-1H-3-benzazepin-7-yl)-imidazolidin-2-one hydrochloride×1.5 water The final ester cleaving is carried out with glacial acetic acid/hydrochloric acid instead of with sodium hydroxide solution.

Calc.: C 60.45 H 6.84 N 9.20 Cl 7.76 Found: 60.45 6.86 9.18 8.09

R_f value: 0.31 (silica gel; methylene chloride/methanol/conc. aqueous ammonia =4:1:0.2)

Mass spectrum: M$^+$=393

EXAMPLE 9

1-[4-(2-Carboxyethyl)phenyl]-3-(2,3,4,5-tetrahydro-1H-3-benzazepin-7-yl)-imidazolidin-2-one 800 mg of 1-[4-[2-(methoxycarbonyl)ethyl]phenyl]-3-(2,3,4,5-tetrahydro-1H-3-benzazepin-7-yl)-imidazolidin-2-one-hydrochloride are stirred with 10 ml of semiconcentrated hydrochloric acid and 10 ml of glacial acetic acid. After 2 hours, a further 5 ml of semiconcentrated hydrochloric acid and 5 ml of glacial acetic acid are added and the mixture is stirred overnight at ambient temperature. The reaction mixture is evaporated down and the residue is suspended in 10 ml of water. A pH of 6 is achieved using 2N sodium hydroxide solution, the solid is suction filtered, washed with ice water and then dried.

Yield: 560 mg (79% of theory),

R_f value: 0.40 (Reversed Phase silica gel; methanol/5% aqueous saline solution=6:4)

Mass spectrum: M$^+$=379

The following compounds are obtained analogously to Example 9:

(1) 1-[4-(2-carboxyethyl)phenyl]-3-(4aRS,6RS,8aRS)-1,2,3,4,4a,5,6,7,8,8a-decahydroisoquinolin-6-yl)imidazolidin-2-one-hydrochloride Isolated as the hydrochloride R_f value: 0.41 (Reversed Phase silica gel; methanol/5% aqueous saline solution=6:4)

Mass spectrum: M$^+$=371

(2) 1-[4-(2-carboxyethyl)phenyl]-3-(3-ethyl-2,3,4,5-tetrahydro-1H-3-benzazepin-7-yl)-imidazolidin-2-one hydrochloride R_f value: 0.36 (Reversed Phase silica gel; methanol/5% aqueous saline solution=6:4)

Mass spectrum: M$^+$=407

(3) 1-[4-(2-carboxyethyl)phenyl]-3-(3-isopropyl-2,3,4,5-tetrahydro-1H-3-benzazepin-7-yl)-imidazolidin-2-one hydrochloride (4) 1-(2-carboxyethyl)-3-[4-(isoquinolin-6-yl)phenyl] imidazolidin-2-one-hydrochloride (5) 1-[4-(2-carboxyethyl)phenyl]-3-(4,4-dimethyl-1,2,3,4-tetrahydroisoquinolin-6-yl)-imidazolidin-2-one-hydrochloride (6) 1-[4-(2-carboxyethyl)phenyl]-3-(3-butyl-2,3,4,5-tetrahydro-1H-3-benzazepin-7-yl)-imidazolidin-2-one-hydrochloride R_f value: 0.33 (Reversed Phase silica gel; methanol/5% aqueous saline solution=6:4)

Mass spectrum: M$^+$=435

(7) 1-[4-(2-carboxyethyl)phenyl]-3-(1-amino-3,4-dihydroisoquinolin-6-yl)-imidazolidin-2-one-hydrochloride (8) 1-[4-(2-carboxyethyl)phenyl]-3-(2-methyl-3,4-dihydroquinazolin-7-yl)-imidazolidin-2-one-hydrochloride (9) 1-[4-(2-carboxyethyl)phenyl]-3-(4,4-dimethyl-3,4-dihydroquinazolin-7-yl)- imidazolidin-2-one-hydrochloride

(10) 3-[trans-4-(2-carboxyethyl)cyclohexyl]-1-(2,3,4,5-tetrahydro-1H-3-benzazepin-7-yl)-hydantoin-hydrochloride Melting point: >250° C.

R_f value: 0.36 (Reversed Phase silica gel; methanol/5% aqueous saline solution=6:4).

Calc.: 60.61 H 6.94 N 9.64 Cl 8.13 Found: 60.45 6.90 9.61 8.28

(11) 1-[trans-4-(2-carboxyethyl)cyclohexyl]-3-(7-ethyl-6,7,8,9-tetrahydro-5H-pyridazino[2,3-d]azepin-2-yl)imidazolidin-2-one×2 HCl×0.9 H$_2$O Melting point: 283°–286° C.

R_f value: 0.46 (Reversed Phase silica gel; methanol/5% aqueous saline solution=6:4).

Calc.: C 52.36 H 7.35 N 13.88 Cl 14.05 Found: 52.70 7.44 13.86 14.01

(12) 1-[trans-4-(2-carboxyethyl)cyclohexyl]-3-(3-ethyl-2,3,4,5-tetrahydro-1H-3-benzazepin-7-yl)-3H-imidazol-2-one-hydrochloride×0.5 H$_2$O R_f value: 0.38 (Reversed Phase silica gel; methanol/5% aqueous saline solution=6:4)

Calc.: C 63.08 H 7.72 N 9.19 Cl 7.76 Found: 63.26 7.69 9.28 7.64

(13) 1-[trans-4-(2-carboxyethyl)cyclohexyl]-3-(2,3,4,5-tetrahydro-1H-3-benzazepin-7-yl)-hydantoin-hydrochloride R_f value: 0.16 (silica gel; methylene chloride/methanol/conc. aqueous ammonia=80:20:2)

Calc.: C 60.61 H 6.94 N 9.64 Cl 8.13 Found: 60.34 6.94 9.58 8.27

(14) 1-[trans-4-(2-carboxyethyl)cyclohexyl]-3-(2,3,4,5-tetrahydro-1H-3-benzazepin-7-yl)-3,4,5,6-tetrahydro-1H-pyrimidin-2-one×1.65 HCl×0.7 H$_2$O Melting point: 230°–235° C.

R_f value: 0.40 (Reversed Phase silica gel/methanol/5% aqueous saline solution=6:4)

Calc.: C 58.27 H 7.71 N 8.86 Cl 12.33 Found: 58.04 7.70 8.82 12.43

(15) 1-(2-carboxyethyl)-3-[4-(3-methyl-2,3,4,5-tetrahydro-1H-3-benzazepin-7-yl)phenyl]-imidazolidin-2-one-hydrochloride Melting point: >250° C.

R_f value: 0.20 (Reversed Phase silica gel/methanol/5% aqueous saline solution=6:4)

(16) 1-[trans-4-(2-carboxyethyl)cyclohexyl]-3-(6,7,8,9-tetrahydro-5H-pyrimido[4,5-d]azepin-2-yl)-imidazolidin-2-one-hydrochloride R_f value: 0.60 (Reversed Phase silica gel/methanol/5% aqueous saline solution=6:4)

(17) 1-[trans-4-(2-carboxyethyl)cyclohexyl]-3-(6,7,8,9-tetrahydro-5H-pyrazino[2,3-d]azepin-2-yl)-imidazolidin-2-one-hydrochloride

(18) 1-[trans-4-(2-carboxymethyl)cyclohexyl]-3-(6,7,8,9-tetrahydro-5H-pyrido[2,3-d]azepin-2-yl)-imidazolidin-2-one-hydrochloride

(19) 1-[trans-4-(2-carboxyethyl)cyclohexyl]-3-(1,2,3,4-tetrahydro-isoquinolin-6-yl)-imidazolidin-2-one-hydrochloride

(20) 1-[trans-4-(2-carboxyethyl)cyclohexyl]-3-(2,3-dimethyl-3,4-dihydroquinazolin-7-yl)-imidazolidin-2-one-hydrochloride

(21) 1-[trans-4-(2-carboxyethyl)cyclohexyl]-3-(3-ethyl-2,3,4,5-tetrahydro-1H-3-benzazepin-7-yl)-imidazolidin-2-one-hydrochloride Melting point: >270° C.

$R_f$ value: 0.35 (Reversed Phase silica gel/methanol/5% aqueous saline solution=6:4)

(22) 1-[trans-4-(2-carboxyethyl)cyclohexyl]-3-(3-propyl-2,3,4,5-tetrahydro-1H-3-benzazepin-7-yl)-imidazolidin-2-one×1.07 HCl×1 H$_2$O Melting point: >250° C.

$R_f$ value: 0.32 (Reversed Phase silica gel/methanol/5% aqueous saline solution=6:4)

Calc.: C 61.96 H 8.33 N 8.67 Cl 7.83 Found: 62.10 8.14 8.77 7.94

(23) 1-[trans-4-(2-carboxyethyl)cyclohexyl]-3-(3-allyl-2,3,4,5-tetrahydro-1H-3-benzazepin-7-yl)-imidazolidin-2-one×1.1 HCl×1.5 H$_2$O Melting point: >250° C.

$R_f$ value: 0.30 (Reversed Phase silica gel/methanol/5% aqueous saline solution=6:4)

Calc.: C 60.94 H 8.00 N 8.53 Cl 7.91 Found: 61.32 7.63 8.47 7.82

(24) 1-[trans-4-(2-carboxyethyl)cyclohexyl]-3-(3-isobutyl-2,3,4,5-tetrahydro-1H-3-benzazepin-7-yl)imidazolidin-2-one-hydrochloride

(25) 1-[trans-4-(2-carboxyethyl)cyclohexyl]-3-[3-(2-hydroxyethyl)-2,3,4,5-tetrahydro-1H-3-benzazepin-7-yl]imidazolidin-2-one-hydrochloride Melting point: 257°–260° C.

$R_f$ value: 0.46 (Reversed Phase silica gel/methanol/5% aqueous saline solution=6:4)

(26) 1-[trans-4-(2-carboxyethyl)cyclohexyl]-3-[3-(carboxymethyl)-2,3,4,5-tetrahydro-1H-3-benzazepin-7-yl]imidazolidin-2-one-hydrochloride Melting point: >280° C.

$R_f$ value: 0.39 (Reversed Phase silica gel/methanol/5% aqueous saline solution=6:4)

(27) 1-[trans-4-(2-carboxyethyl)cyclohexyl]-3-(3-benzyl-2,3,4,5-tetrahydro-1H-3-benzazepin-7-yl)-imidazolidin-2-one-hydrochloride Melting point: >250° C.

$R_f$ value: 0.21 (Reversed Phase silica gel/methanol/5% aqueous saline solution=6:4)

(28) 1-[trans-4-(2-carboxyethyl)cyclohexyl]-3-[3-(cyclopropylmethyl)-2,3,4,5-tetrahydro-1H-3-benzazepin-7-yl]imidazolidin-2-one-hydrochloride Melting point: >280° C.

$R_f$ value: 0.31 (Reversed Phase silica gel/methanol/5% aqueous saline solution=6:4)

(29) 1-[trans-4-(2-carboxyethyl)cyclohexyl]-3-(3-cyclopropyl-2,3,4,5-tetrahydro-1H-3-benzazepin-7-yl)imidazolidin-2-one-hydrochloride

(30) 1-[trans-4-(2-carboxyethyl)cyclohexyl]-3-[3-(cyclohexylmethyl)-2,3,4,5-tetrahydro-1H-3-benzazepin-7-yl]-imidazolidin-2-one-hydrochloride

(31) 1-[trans-4-(2-carboxyethyl)cyclohexyl]-3-(3-cyclohexyl-2,3,4,5-tetrahydro-1H-3-benzazepin-7-yl)imidazolidin-2-one-hydrochloride

EXAMPLE 10

1-[4-[2-(Methoxycarbonyl)ethyl]phenyl]-3-(2,3,4,5-tetrahydro-1H-3-benzazepin-7-yl)-imidazolidin-2-one-hydrochloride 2.3 g of 1-(3-tert. Butyloxycarbonyl-2,3,4,5-tetrahydro-1H-3-benzazepin-7-yl)-3-[4-[2-(methoxycarbonyl)ethyl]phenyl]-imidazolidin-2-one are stirred in 30 ml of methanolic hydrochloric acid for 2 hours at ambient temperature. The reaction mixture is evaporated down, the residue is stirred with ice water, suction filtered, washed with a little methanol and tert.butyl-methylether and then dried.

Yield: 1.8 g (90% of theory),

Calc.: C 64.25 H 6.56 N 9.77 Cl 8.25 Found: 64.08 6.60 9.92 8.51

$R_f$ value: 0.26 (Reversed Phase silica gel; methanol/5% aqueous saline solution=6:4)

Mass spectrum: M$^+$=393

EXAMPLE 11

1-[(4aRS,6RS,8aRS)-1,2,3,4,4a,5,6,7,8,8a-Decahydroisoquinolin-6-yl]-3-[4-[2-(methoxycarbonyl)ethyl]phenyl]-imidazolidin-2-one-hydrochloride To 216 mg of 1-[4-[2-(methoxycarbonyl)ethyl]phenyl]-3-[(4aRS,6RS,8aRS)-2-methyl-1,2,3,4,4a,5,6,7,8,8a-decahydroisoquinolin-6-yl]-imidazolidin-2-one and 185 mg of 1,8-bis-(dimethylamino)-naphthaline in 5 ml of 1,2-dichloroethane are added 0.09 ml of 1-chloroethylchloroformate, the mixture is stirred for 20 minutes at ambient temperature and then refluxed for 2.5 hours. The reaction mixture is evaporated down, the residue is combined with 10 ml of methanol and refluxed for 3 hours. The reaction mixture is acidified with methanolic hydrochloric acid, evaporated down and purified by chromatography over a silica gel column using methylene chloride/methanol (92:8).

Yield: 200 mg (87% of theory), $R_f$ value: 0.35 (Reversed Phase silica gel; methanol/5% aqueous saline solution=6:4)

EXAMPLE 12

1-[4-[2-(Methoxycarbonyl)ethyl]phenyl]-3-[(4aRS,6RS,8aRS)-2-methyl-1,2,3,4,4a,5,6,7,8,8a-decahydroisoquinolin-6-yl]-imidazolidin-2-one 950 mg of 1-[4-[2-(methoxycarbonyl)ethyl]phenyl]-3-[(4aRS,6RS,8aRS)-2-methyl-1,2,3,4,4a,5,6,7,8,8a-decahydroisoquinolin-6-yl]-3H-imidazol-2-one in 50 ml of ethyl acetate are hydrogenated in the presence of palladium on activated charcoal for 5 hours under a hydrogen pressure of 50 psi at ambient temperature and then for 5 hours at 50° C. The catalyst is filtered off and the filtrate is evaporated down. The residue is briefly heated with tert.butylmethylether, then cooled with stirring. The solid is suction filtered, washed with tert.butylmethylether and dried.

Yield: 300 mg (31% of theory),

Melting point: 155°–157° C.

$R_f$ value: 0.29 (Reversed Phase silica gel; methanol/5% aqueous saline solution=6:4)

The following compounds are obtained analogously to Example 12:

(1) 1-[trans-4-[2-(methoxycarbonyl)ethyl]cyclohexyl]-3-(3-trifluoroacetyl-2,3,4,5-tetrahydro-1H-3-benzazepin-7-yl)-imidazolidin-2-one Melting point: 165°–168° C.

$R_f$ value: 0.44 (silica gel; cyclohexane/ethyl acetate=1:1)

(2) 1-trans-4-[[(methoxycarbonyl)methyl]oxy]cyclohexyl]-3-(3-trifluoroacetyl-2,3,4,5-tetrahydro-1H-3-benzazepin-7-yl)-imidazolidin-2-one Melting point: 146°–147° C.

$R_f$ value: 0.62 (silica gel; ethyl acetate/cyclohexane=3:1)

(3) 1-[4-[2-(ethoxycarbonyl)-1-propyl]phenyl]-3-(3-trifluoroacetyl-2,3,4,5-tetrahydro-1H-3-benzazepin-7-yl)-3H-imidazolidin-2-one $R_f$ value: 0.32 (silica gel; cyclohexane/ethyl acetate=2:1)

(4) 1-[2-[4-(methoxycarbonyl)phenyl]ethyl]-3-(3-trifluoroacetyl-2,3,4,5-tetrahydro-1H-3-benzazepin-7-yl)-imidazolidin-2-one Melting point: 143°–144° C.

49

$R_f$ value: 0.46 (silica gel; cyclohexane/ethyl acetate=1:1)

(5) 1-[trans-4-[2-(methoxycarbonyl)ethyl]cyclohexyl]-3-(3-ethyl-2,3,4,5-tetrahydro-1H-3-benzazepin-7-yl)imidazolidin-2-one-hydrochloride Melting point: from 230° C. (Decomp.)

$R_f$ value: 0.22 (Reversed Phase silica gel; methanol/5% aqueous saline solution=6:4)

(6) 1-[trans-4-[2-(methoxycarbonyl)ethyl]cyclohexyl]-3-(7-ethyl-6,7,8,9-tetrahydro-5H-pyrazino[2,3-d]azepin-2-yl)-imidazolidin-2-one Melting point: 136°–138° C.

$R_f$ value: 0.33 (silica gel; methylene chloride/methanol =9:1)

(7) 1-[4-[2-(ethoxycarbonyl)-1-phenyl-ethyl]phenyl]-3-(3-trifluoroacetyl-2,3,4,5-tetrahydro-1H-benzazepin-7-yl)-imidazolidin-2-one $R_f$ value: 0.22 (silica gel; cyclohexane/ethyl acetate=7:3)

EXAMPLE 13

1-[4-[2-(Methoxycarbonyl)ethyl]phenyl]-3-[(4aRS,6RS,8aRS)-2-methyl-1,2,3,4,4a,5,6,7,8,8a-decahydroisoquinolin-6-yl]-3H-imidazol-2-one To 6.9 g of (4aRS,6RS,8aRS)-6-[(2,2-dimethoxyethyl)amino]-2-methyl-1,2,3,4,4a,5,6,7,8,8a-decahydroisoquinoline in 30 ml of dioxane are added 6.4 g of 4-[2-(methoxycarbonyl)ethyl]-phenylisocyanate and the mixture is stirred for 2 hours at ambient temperature. The reaction mixture is evaporated down, taken up in 100 ml of methanol, mixed with methanolic hydrochloric acid and refluxed for 20 minutes. The reaction mixture is evaporated down and the residue is stirred with 200 ml of water. The precipitate is removed by suction filtering and the filtrate is extracted with ethyl acetate. The organic phase is discarded. The aqueous phase is made alkaline with potassium carbonate solution and extracted several times with ethyl acetate. The combined ethyl acetate extracts are washed once with saturated saline solution, dried and evaporated down. The crude product is purified by chromatography over an aluminium oxide column (basic) with ethyl acetate followed by trituration with tert.butylmethylether.

Yield: 1.03 g (9% of theory), $R_f$ value: 0.55 (silica gel; toluene/dioxane/methanol/conc. aqueous ammonia 20:50:20:5)

The following compounds are obtained analogously to Example 13:

(1) 1-[4-[2-(methoxycarbonyl)ethyl]phenyl]-3-[(4aRS,6SR,8aRS)-2-methyl-1,2,3,4,4a,5,6,7,8,8a-decahydroisoquinolin-6-yl]-3H-imidazol-2-one×0.3 water Melting point: 140°–145° C.

Calc.: C 68.56 H 7.91 N 10.43 Found: 68.49 7.97 10.51

(2) 1-[2-[4-(methoxycarbonyl)phenyl]ethyl]-3-(3-trifluoroacetyl-2,3,4,5-tetrahydro-1H-3-benzazepin-7-yl)-3H-imidazol-2-one Amine and isocyanate are stirred in dioxane first at ambient temperature and then over a steam bath. The treatment with methanolic hydrochloric acid is omitted. The [2-[4-(methoxycarbonyl)phenyl]ethyl]-isocyanate used is obtained by reacting the corresponding amine-hydrochloride with phosgene.

Melting point: 165°–167° C.

$R_f$ value: 0.31 (silica gel; cyclohexane/ethyl acetate=1:1).

50

EXAMPLE 14

4-[4-[2-(Carboxyethyl)phenyl]-5-methyl-2-(2,3,4,5-tetrahydro-1H-3-benzazepin-7-yl)-4H-1,2,4-triazol-3-one-hydrochloride-hydrate 410 mg of 4-[4-[2-(methoxycarbonyl)ethyl]phenyl]-5-methyl-2-(3-trifluoroacetyl-2,3,4,5-tetrahydro-1H-3-benzazepin-7-yl)-4H-1,2,4-triazol-3-one are stirred with 10 ml glacial acetic acid and 10 ml of semiconcentrated hydrochloric acid for 7 hours at 90° C. After cooling, the mixture is evaporated down, the residue is stirred with water, suction filtered and washed with water and acetone.

Yield: 240 mg (57% of theory),

Melting point: >250° C.

$R_f$ value: 0.43 (Reversed Phase silica gel; methanol/5% aqueous saline solution=6:4)

Calc.: C 59.12 H 6.09 N 12.53 Cl 7.93 Found: 58.96 6.13 12.31 7.74

The following compounds are obtained analogously to Example 14:

(1) 1-[trans-4-(2-carboxyethyl)cyclohexyl]-3-(2,3,4,5-tetrahydro-1H-3-benzazepin-7-yl)-imidazolidin-2-one-hydrochloride Melting point: >250° C.

$R_f$ value: 0.46 (Reversed Phase silica gel; methanol/5% aqueous saline solution=6:4)

Calc.: C 62.62 H 7.64 N 9.98 Cl 8.40 Found: 62.24 7.67 10.01 8.86

(2) 1-[trans-4-(2-carboxyethyl)cyclohexyl]-3-(1,2,3,4,5,6-hexahydro-3-benzazocin-8-yl)-imidazolidin-2-one-hydrochloride (3) 2-[4-(2-carboxyethyl)phenyl]-4-(2,3,4,5-tetrahydro-1H-3-benzazepin-7-yl)-4H-1,2,4-triazol-3-one-hydrochloride (4) 4-[4-(2-carboxyethyl)phenyl]-5-phenyl-2-(2,3,4,5-tetrahydro-1H-3-benzazepin-7-yl)-4H-1,2,4-triazol-3-one-hydrochloride (5) 4-[4-(2-carboxyethyl)phenyl]-2-(2,3,4,5-tetrahydro-1H-3-benzazepin-7-yl)-5-trifluoromethyl-4H-1,2,4-triazol-3-one-hydrochloride (6) 1-[4-(2-carboxyethyl)phenyl]-3-(2,3,4,5-tetrahydro-1H-3-benzazepin-7-yl)-3,4,5,6-tetrahydro-1H-pyrimidin-2-one-hydrochloride (7) 4-[4-(2-carboxyethyl)phenyl]-5-ethyl-2-(2,3,4,5-tetrahydro-1H-3-benzazepin-7-yl)-4H-1,2,4-triazol-3-one-hydrochloride (8) 5-[4-(2-carboxyethyl)phenyl]-4-methyl-2-(2,3,4,5-tetrahydro-1H-3-benzazepin-7-yl)-4H-1,2,4-triazol-3-one-hydrochloride (9) 4-[4-(2-carboxyethyl)phenyl]-3-methyl-1-(1,2,3,4-tetrahydroisoquinolin-6-yl)-imidazolidin-2-one-hydrochloride

(10) 2-[trans-4-(2-carboxyethyl)cyclohexyl]-4-(2,3,4,5-tetrahydro-1H-3-benzazepin-7-yl)-2H,4H-1,2,4-triazol-3,5-dione-hydrochloride

(11) 1-[3-(2-carboxyethyl)phenyl]-3-(2,3,4,5-tetrahydro-1H-3-benzazepin-7-yl)-imidazolidin-2-one-hydrochloride

(12) 1-[4-(carboxymethyl)phenyl]-3-(2,3,4,5-tetrahydro-1H-3-benzazepin-7-yl)-imidazolidin-2-one-hydrochloride

(13) 2-[trans-4-(2-carboxyethyl)cyclohexyl]-5-(2,3,4,5-tetrahydro-1H-3-benzazepin-7-yl)-3,4-dihydro-2H,5H-1,2,5-thiadiazol-1,1-dioxide $R_f$ value: 0.50 (Reversed phase silica gel; methanol/5% aqueous saline solution=6:4)

(14) 1-[4-(2-carboxy-1-octyl)phenyl]-3-(2,3,4,5-tetrahydro-1H-3-benzazepin-7-yl)-imidazolidin-2-one-hydrochloride

(15) 2-[trans-4-(2-carboxyethyl)cyclohexyl]-4-(2,3,4,5-tetrahydro-1H-3-benzazepin-7-yl)-1-methyl-2H,4H-1,2,4-triazol-3,5-dione-hydrochloride

(16) 1-[4-(3-carboxypropyl)phenyl]-3-(2,3,4,5tetrahydro-1H-3-benzazepin-7-yl)-imidazolidin-2-one-hydrochloride

(17) 1-(5-carboxypentyl)-3-(2,3,4,5-tetrahydro-1H-3-benzazepin-7-yl)-imidazolidin-2-one-hydrochloride

(18) 1-[4-(2-carboxyethyl)-2-fluorophenyl]-3-(2,3,4,5-tetrahydro-1H-3-benzazepin-7-yl)-imidazolidin-2-one-hydrochloride

(19) 1-[4-(2-carboxyethyl)-3-methyl-phenyl]-3-(2,3,4,5-tetrahydro-1H-3-benzazepin-7-yl)-imidazolidin-2-one-hydrochloride

(20) 1-[trans-4-[(carboxymethyl)oxy]cyclohexyl]-3-(2,3,4,5-tetrahydro-1H-3-benzazepin-7-yl)-imidazolidin-2-one-hydrochloride Melting point: 316°–317° C. (Decomp.)

$R_f$ value: 0.66 (Reversed Phase silica gel; methanol/5% aqueous saline solution=6:4)

Calc.: C 59.50 H 7.13 N 9.91 Cl 8.36 Found: 59.26 7.13 9.94 8.44

(21) 1-[4-(trans-2-carboxyethenyl)phenyl]-3-(2,3,4,5-tetrahydro-1H-3-benzazepin-7-yl)-imidazolidin-2-one-hydrochloride $R_f$ value: 0.64 (Reversed Phase silica gel; methanol/5% aqueous saline solution=6:4)

Mass spectrum: $M^+=377$

(22) 1-[4-(2-carboxy-1-propyl)phenyl]-3-(2,3,4,5-tetrahydro-1H-3-benzazepin-7-yl)-imidazolidin-2-one-hydrochloride $\times H_2O$ $R_f$ value: 0.34 (Reversed Phase silica gel; methanol/5% aqueous saline solution=6:4)

Calc.: C 61.66 H 6.71 N 9.38 Cl 7.91 Found: 61.56 6.75 9.30 8.14

(23) 1-trans-4-(2-carboxyethyl) cyclohexyl]-3-(2,3,4,5-tetrahydro-ill-3-benzazepin-7-yl)-3H-imidazol-2-one-hydrochloride

(24) 1-[trans-4-(2-carboxyethyl)cyclohexyl]-3-(2,3,4,5-tetrahydro-1H-2-benzazepin-7-yl)-imidazolidin-2-one-hydrochloride

(25) 2-[trans-4-(2-carboxyethyl)cyclohexyl]-4-(2,3,4,5-tetrahydro-1H-3-benzazepin-7-yl)-4H-1,2,4-triazol-3-one-hydrochloride 2N hydrochloric acid and as starting material: the compound of example 18(1) are used.

Melting point: >220° C.

$R_f$ value: 0.50 (Reversed Phase silica gel; methanol/5% aqueous saline solution=6:4)

Calc.: C 59.92 H 6.94 N 13.31 Cl 8.42 Found: 60.03 6.99 13.32 8.46

(26) 2-[trans-4-(2-carboxyethyl)cyclohexyl]-4-(2,3,4,5-tetrahydro-1H-3-benzazepin-7-yl)-5-methyl-4H-1,2,4-triazol-3-one-hydrochloride

(27) 2-[trans-4-(2-carboxyethyl)cyclohexyl]-4-(2,3,4,5-tetrahydro-1H-3-benzazepin-7-yl)-5-Phenyl-4H-1,2,4-triazol-3-one-hydrochloride

(28) 4-[trans-4-(2-carboxyethyl)cyclohexyl]-2-(2,3,4,5-tetrahydro-1H-3-benzazepin-7-yl)-4H-1,2,4-triazol-3-one-hydrochloride Melting point: >240° C.

$R_f$ value: 0.64 (Reversed Phase silica gel; methanol/5% aqueous saline solution=6:4)

(29) 4-[trans-4-(2-carboxyethyl)cyclohexyl]-2-(2,3,4,5-tetrahydro-1H-3-benzazepin-7-yl)-5-methyl-4H-1,2,4-triazol-3-one-hydrochloride $R_f$ value: 0.48 (Reversed Phase silica gel; methanol/5% aqueous saline solution=6:4)

Calc.: C 60.75 H 7.18 N 12.88 Cl 8.15 Found: 60.54 7.26 12.68 8.54

(30) 4-[trans-4-(2-carboxyethyl)cyclohexyl]-2-(2,3,4,5-tetrahydro-1H-3-benzazepin-7-yl)-5-phenyl-4H-1,2,4-triazol-3-one-hydrochloride

(31) 1-[4-(2-carboxy-1-phenyl-ethyl)phenyl]-3-(2,3,4,5-tetrahydro-1H-3-benzazepin-7-yl)-imidazolidin-2-one-hydrochloride $R_f$ value: 0.31 (Reversed Phase silica gel; methanol/5% aqueous saline solution=6:4)

(32) 1-[1-(2-carboxyethyl)piperidin-4-yl]-3-(2,3,4,5-tetrahydro-1H-3-benzazepin-7-yl)-imidazolidin-2-one-hydrochloride

(33) 1-(trans-4-carboxycyclohexyl)-3-[2-(2,3,4,5-tetrahydro-1H-3-benzazepin-7-yl)ethyl]-imidazolidin-2-one-hydrochloride

(34) 1-[2-(4-carboxyphenyl)ethyl]-3-(2,3,4,5-tetrahydro-1H-3-benzazepin-7-yl)-imidazolidin-2-one-hydrochloride$\times H_2O$ $R_f$ value: 0.40 (Reversed Phase silica gel; methanol/5% aqueous saline solution=6:4)

Mass spectrum: $M^+=379$

Calc.: C 60.89 H 6.50 N 9.68 Cl 8.17 Found: 60.57 6.62 9.77 8.22

EXAMPLE 15

4-[4-[2-(Methoxycarbonyl) ethyl]phenyl]-5-methyl-2-(3-trifluoroacetyl-2,3,4,5-tetrahydro-1H-3-benzazepin-7-yl)-4H-1, 2,4-triazol-3-one 1.6 g of 7-iodo-3-trifluoroacetyl-2,3,4,5-tetrahydro-1H-3-benzazepine, 1.1 g of 4-[4-[2-(methoxycarbonyl)ethyl]phenyl]-5-methyl-4H-1,2,4-triazol-3-one, 0.19 ml of tris-[2-(2-methoxyethoxy)-ethyl]-amine, 130 mg of copper(I)chloride, 130 mg of copper(I)iodide and 1.1 g of potassium carbonate are refluxed for 2 hours in 30 ml of dimethylformamide. After cooling, the mixture is evaporated down and the residue is divided between water and methylene chloride. The solid is suction filtered, the organic phase is separated off, washed with water, dried, filtered and evaporated down. The residue is purified by chromatography over a silica gel column using cyclohexane/ethyl acetate=1:1.

Yield: 340 mg (16% of theory),

Melting point: 160°–162° C.

$R_f$ value: 0.51 (silica gel; cyclohexane/ethyl acetate=1:1)

The following compounds are obtained analogously to Example 15:

(1) 4-[trans-4-[2-(methoxycarbonyl)ethyl]cyclohexyl]-2-(3-trifluoroacetyl-2,3,4,5-tetrahydro-1H-3-benzazepin-7-yl)-5-methyl-4H-1,2,4-triazol-3-one Melting point: 175°–177° C.

$R_f$ value: 0.50 (silica gel; methylene chloride/ethyl acetate=90:10)

(2) 4-[trans-4-[2-(methoxycarbonyl)ethyl]cyclohexyl]-2-(3-trifluoroacetyl-2,3,4,5-tetrahydro-1H-3-benzazepin-7-yl)-4H-1,2,4-triazol-3-one $R_f$ value: 0.40 (silica gel; methylene chloride/methanol =100:1)

EXAMPLE 16

1-[trans-4-[2-(Methoxycarbonyl)ethyl]cyclohexyl]-3-(3-trifluoroacetyl-2,3,4,5-tetrahydro-1H-3-benzazepin-7-yl)-hydantoin To 4.1 g of (3-trifluoroacetyl-2,3,4,5-tetrahydro-1H-3-benzazepin-7-yl)-isocyanate and 3.7 g of methyl [[trans-4-[2-(methoxycarbonyl)-ethyl]cyclohexyl]amino]-acetate-hydrochloride in 50 ml of acetonitrile are added 3.2 ml of N-ethyl-diisopropylamine and the mixture is stirred for 2 ½ days at ambient temperature. The reaction mixture is evaporated down, the residue is taken up in ethyl acetate and washed with water and saline solution. The organic phase is dried and evaporated down and the residue is crystallised with a little methanol in an ice bath. The product is suction filtered, washed with cold methanol and dried.

Yield: 4.1 g (56% of theory),
Melting point: 118°–120° C.
$R_f$ value 0.85 (silica gel; ethyl acetate)

EXAMPLE 17

1-[trans-4-[2-(Isopropoxycarbonyl)ethyl]cyclohexyl]-3-(3-propyl-2,3,4,5-tetrahydro-1H-3-benzazepin-7-yl)imidazolidin-2-one-hydrochloride 230 mg of 1-[trans-4-[2-(isopropoxycarbonyl)ethyl]cyclohexyl]-3-(3-allyl-2,3,4,5-tetrahydro-1H-3-benzazepin-7-yl)-imidazolidin-2-one-hydrochloride are hydrogenated in 10 ml of isopropanol at 30° C. under a hydrogen pressure of 50 psi in the presence of 50 mg of 10% palladium on activated charcoal for 6 hours. The catalyst is suction filtered and the filtrate is evaporated down.

Yield: 240 mg,
$R_f$ value 0.55 (silica gel; methylene chloride/methanol/conc. aqueous ammonia=95:5:1)

EXAMPLE 18

2-[trans-4-[2-(Methoxycarbonyl)ethyl]cyclohexyl]-5-(3-trifluoroacetyl-2,3,4,5-tetrahydro-1H-3-benzazepin-7-yl)-3,4-dihydro-2H,5H-1,2,5-thiadiazol-1,1-dioxide To 1.25 g of 2-(3-trifluoroacetyl-2,3,4,5-tetrahydro-1H-3-benzazepin-7-yl)-3,4-dihydro-2H,5H-1,2,5-thiadiazol-1,1-dioxide, 0.64 g of methyl 3-(cis-4-hydroxycyclohexyl)propionate [$R_f$ value: 0.58 (silica gel; cyclohexane/ethyl acetate=1:1); isolated from the cis/trans mixture by chromatography over a silica gel column using cyclohexane/ethyl acetate (1:1)] and 0.90 g triphenylphosphine in 2 ml of acetonitrile, are added 0.54 ml of diethyl azodicarboxylate. A further 1.5 g of methyl 3-(cis-4-hydroxycyclohexyl)propionate and a mixture of 0.90 g of triphenylphosphine and 0.54 ml of diethyl azodicarboxylate in 2 ml of acetonitrile are added. After 30 minutes stirring at ambient temperature, a mixture of 0.90 g of triphenylphosphine and 0.54 ml of diethyl azodicarboxylate is added once more. After stirring at ambient temperature overnight, the mixture is evaporated down and the residue is purified by chromatography over a silica gel column with cyclohexane/ethyl acetate/methylene chloride (1:1:1).

Yield: 700 mg (38% of theory),
Melting point: 169°–173° C.
$R_f$ value: 0.61 (silica gel; cyclohexane/ethyl acetate/methylene chloride=1:1:1)

The following compound is obtained analogously to example 18:

(1)-2[trans-4-[2-(Methoxycarbonyl)ethyl]cyclohexyl]-4-(3-tert.butyloxycarbonyl-2,3,4,5-tetrahydro-1H-3-benzazepine-7-yl)-4H-1,2,4-triazol-3-one Melting point: 162°–164° C.
$R_f$ value: 0.43 (silica gel; cyclohexane/ethyl acetate/methylene chloride=1:1:1)

EXAMPLE 19

1-[trans-4-(2-Carboxyethyl)cyclohexyl]-3-(3-methyl-2,3,4,5-tetrahydro-1H-3-benzazepin-7-yl)-imidazolidin-2-one-hydrochloride To a mixture of 5.0 g of 1-[trans-4-(2-carboxyethyl)cyclohexyl]-3-(2,3,4,5-tetrahydro-1H-3-benzazepin-7-yl)-imidazolidin-2-one-hydrochloride, 4.5 ml of formic acid, 3.6 ml of 37% aqueous formaldehyde and 20 ml of water are added 2.0 g of sodium hydrogen carbonate, whilst cooling with ice, and the mixture is then heated to 65° C. After 8 hours it is cooled, stirred overnight and the mixture is evaporated down. The residue is stirred with water and evaporated down once again. Then the residue is stirred with water once more and adjusted to a pH of 1 using hydrochloric acid. It is evaporated down, the residue is stirred with a little water and suction filtered. The filter cake is stirred with acetone, the product is suction filtered, washed with acetone and dried in vacuo.

Yield: 3.7 g (71% of theory),
Melting point: 292°–295° C. (Decomp.)
$R_f$ value: 0.38 (Reversed Phase silica gel; methanol/5% aqueous saline solution=6:4)

The following compounds are obtained analogously to Example 19:

(1) 1-[trans-4-[(carboxymethyl)oxy]cyclohexyl]-3-(3-methyl-2,3,4,5-tetrahydro-1H-3-benzazepin-7-yl)imidazolidin-2-one-hydrochloride×NaCl×0.5 $H_2O$ $R_f$ value: 0.62 (Reversed Phase silica gel; methanol/5% aqueous saline solution=6:4)

Calc.: C 52.28 H 6.58 N 8.31 Cl 13.49 Found: 52.28 6.68 8.33 14.03

(2) 1-[4-(2-carboxy-1-propyl)phenyl]-3-(3-methyl-2,3,4,5-tetrahydro-1H-3-benzazepin-7-yl)-imidazolidin-2-one-hydrochloride×0.5

$R_f$ value: 0.29 (Reversed Phase silica gel; methanol/5% aqueous saline solution=6:4)

Calc.: C 63.63 H 6.90 N 9.28 Cl 7.83 Found: 63.32 6.99 9.32 7.81

(3) 3-[trans-4-(2-carboxyethyl)cyclohexyl]-1-(3-methyl-2,3,4,5-tetrahydro-1H-3-benzazepin-7-yl)-hydantoin-hydrochloride Melting point: >250° C.
$R_f$ value: 0.32 (Reversed Phase silica gel; methanol/5% aqueous saline solution=6:4)

Calc.: C 61.39 H 7.17 N 9.34 Cl 7.88 Found: 61.39 7.25 9.37 7.92

(4) 1-[trans-4-(2-carboxyethyl)cyclohexyl]-3-(3-methyl-2,3,4,5-tetrahydro-1H-3-benzazepin-7-yl)-hydantoin-hydrochloride $R_f$ value: 0.37 (silica gel; methylene chloride/methanol/conc. aqueous ammonia=80:20:2)

Calc.: C 61.39 H 7.17 N 9.34 Cl 7.88 Found: 61.11 7.26 9.36 7.86

(5) 2-[trans-4-(2-carboxyethyl)cyclohexyl]-4-(3-methyl-2,3,4,5-tetrahydro-1H-3-benzazepin-7-yl)-1-methyl-2H,4H-1,2,4-triazol-3,5-dione-hydrochloride (6) 2-[trans-4-(2-carboxyethyl)cyclohexyl]-4-(3-methyl-2,3,4,5-tetrahydro-1H-3-benzazepin-7-yl)-4H-1,2,4-triazol-3-one-hydrochloride×1,1 water Melting point: >220° C.
$R_f$ value: 0.48 (Reversed phase silica gel; methanol/5% aqueous saline solution=6.4))

Calc.: C 58.10 H 7.36 N 12.32 Cl 7.80 Found: 58.07 7.36 12.28 7.83

(7) 2-[trans-4-(2-carboxyethyl)cyclohexyl]-4-(3-methyl-2,3,4,5-tetrahydro-1H-3-benzazepin-7-yl)-5-methyl-4H-1,2,4-triazol-3-one-hydrochloride (8) 2-[trans-4-(2-carboxyethyl)cyclohexyl]-4-(3-methyl-2,3,4,5-tetrahydro-1H-3-benzazepin-7-yl)-5-phenyl-4H-1,2,4-triazol-3-one-hydrochloride (9) 4-[trans-4-(2-carboxyethyl)cyclohexyl]-2-(3-methyl-2,3,4,5-tetrahydro-1H-3-benzazepin-7-yl)-4H-1,2,4-triazol-3-one-hydrochloride

(10) 4-[trans-4-(2-carboxyethyl)cyclohexyl]-2-(3-methyl-2,3,4,5-tetrahydro-1H-3-benzazepin-7-yl)-5-methyl-4H-1,2,4-triazol-3-one×1.1 HCl×0.2 $H_2O$ Melting point: 238°–240° C.

R$_f$ value: 0.37 (Reversed Phase silica gel; methanol/5% aqueous saline solution=6:4)

Calc.: C 60.55 H 7.40 N 12.28 Cl 8.55 Found: 60.68 7.53 12.31 8.36

(11) 4-[trans-4-(2-carboxyethyl)cyclohexyl]-2-(3-methyl-2,3,4,5-tetrahydro-1H-3-benzazepin-7-yl)-5-phenyl-4H-1,2,4-triazol-3-one-hydrochloride

(12) 1-[trans-4-(2-carboxyethyl) cyclohexyl]-3-(3-methyl-2,3,4,5-tetrahydro-1H-3-benzazepin-7-yl)-3,4,5,6-tetrahydro-1H-pyrimidin-2-one×1.05 HCl×0.3 H$_2$O Melting point: 237°–240° C.

R$_f$ value: 0.37 (Reversed Phase silica gel; methanol/5% aqueous saline solution=6:4)

Calc.: C 63.04 H 8.07 N 9.18 Cl 8.14 Found: 62.97 8.05 9.15 8.16

(13) 1-[4-(2-carboxy-1-phenyl-ethyl)phenyl]-3-(3-methyl-2,3,4,5-tetrahydro-1H-3-benzazepin-7-yl)-imidazolidin-2-one-hydrochloride

(14) 1-[1-(2-carboxyethyl)piperidin-4-yl]-3-(3-methyl-2,3,4,5-tetrahydro-1H-3-benzazepin-7-yl)-imidazolidin-2-one-hydrochloride

(15) 1-(trans-4-carboxycyclohexyl)-3-[2-(3-methyl-2,3,4,5-tetrahydro-1H-3-benzazepin-7-yl)ethyl]imidazolidin-2-one-hydrochloride

(16) 1-[2-(4-carboxyphenyl)ethyl]-3-(3-methyl-2,3,4,5-tetrahydro-1H-3-benzazepin-7-yl)-imidazolidin-2-one-hydrochloride

(17) 1-[trans-4-(2-carboxyethyl)cyclohexyl]-3-(7-methyl-6,7,8,9-tetrahydro-5H-pyrimido[4,5-d]azepin-2-yl)imidazolidin-2-one-hydrochloride R$_f$ value: 0.56 (Reversed phase silica gel; methanol/5% aqueous saline solution=6.4)

Mass spectrum: M+=401

(18) 1-[trans-4-(2-carboxyethyl)cyclohexyl]-3-(7-methyl-6,7,8,9-tetrahydro-5H-pyrazino[2,3-d]azepin-2-yl)imidazolidin-2-one-hydrochloride

(19) 1-[trans-4-(2-carboxyethyl)cyclohexyl]-3-(7-methyl-6,7,8,9-tetrahydro-5H-pyrido[2,3-d]azepin-2-yl)imidazolidin-2-one-hydrochloride

(20) 1-[trans-4-(2-carboxyethyl)cyclohexyl]-3-(2-methyl-1,2,3,4-tetrahydro-isoquinolin-6-yl)-imidazolidin-2-one-hydrochloride

(21) 1-[trans-4-(2-carboxyethyl)cyclohexyl]-3-(2-methyl-2,3,4,5-tetrahydro-1H-2-benzazepin-7-yl)-imidazolidin-2-one-hydrochloride

(22) 1-[trans-4-(2-carboxethyl)cyclohexyl]-3-(3-methyl-1,2,3,4,5,6-hexahydro-3-benzazocin-8-yl)-imidazolidin-2-one-hydrochloride

(23) 2-[trans-4-(2-carboxyethyl)cyclohexyl]-4-(3-methyl-2,3,4,5-tetrahydro-1H-3-benzazepin-7-yl)-2H,4H-1,2,4-triazol-3,5-dione-hydrochloride

EXAMPLE 20

1-(3-Ethyl-2,3,4,5-tetrahydro-1H-3-benzazepin-7-yl)-3-[4-[2-(methoxycarbonyl)ethyl]phenyl-imidazolidin-2-one 600 mg of 1-[4-[2-(methoxycarbonyl)ethyl]phenyl]-3-(2,3,4,5-tetrahydro-1H-3-benzazepin-7-yl)-imidazolidin-2-one-hydrochloride and 128 mg of sodium hydride (55% in paraffin oil) are treated in 15 ml of dimethylformamide in an ultrasound bath for 2.5 hours. 125 μl of ethyliodide are added and the mixture is treated for a further 2.5 hours. The reaction mixture is combined with 50 ml of water, the precipitate is suction filtered, washed with water and dried. The crude product is purified by chromatography over a silica gel column using methylene chloride/methanol/conc. aqueous ammonia (9:1:0.1).

Yield: 260 mg (44% of theory),

Melting point: 168°–170° C.

R$_f$ value: 0.45 (silica gel; methylene chloride/methanol/conc. aqueous ammonia =4:1:0,2)

The following compounds are obtained analogously to Example 20:

(1) 1-(3-butyl-2,3,4,5-tetrahydro-1H-3-benzazepin-7-yl)-3-[4-[2-(methoxycarbonyl) ethyl]phenyl]-imidazolidin-2-one R$_f$ value: 0.64 (silica gel; methylene chloride/methanol/conc. aqueous ammonia=4:1:0.2)

(2) 1-[trans-4-[2-(isopropoxycarbonyl)ethyl]cyclohexyl] 3-(3-allyl-2,3,4,5-tetrahydro-1H-3-benzazepin-7-yl)imidazolidin-2-one-hydrochloride Carried out with allylbromide/N-ethyl-diisopropylamine in acetonitrile R$_f$ value: 0.63 (silica gel; methylene chloride/methanol/conc. aqueous ammonia=95:5:1)

(3) 1-[trans-4-[2-(methoxycarbonyl) ethyl]cyclohexyl]-3-(3-benzyl-2,3,4,5-tetrahydro-1H-3-benzazepin-7-yl)imidazolidin-2-one-hydrochloride R$_f$ value: 0.30 (silica gel; methylene chloride/methanol= 95:5)

(4) 1-[trans-4-[2-(methoxycarbonyl)ethyl]cyclohexyl]-3-(3-benzyl-2,3,4,5-tetrahydro-1H-3-benzazepin-7-yl)imidazolidin-2-one-hydrojodide Acetonitrile and cyclopropylmethylbromide in the presence of sodium jodide and N-ethyl-diisopropylamine are used.

Melting point: 225°–230° C. (decomp.)

R$_f$ value: 0.72 (silica gel; methylene chloride/methanol/conc. aqueous ammonia=90:10:2)

(5) 1-[trans-4-[2-(methoxycarbonyl)ethyl]cyclohexyl]-3-(2-hydroxyethyl)-2,3,4,5-tetrahydro-1H-3-benzazepin-7-yl)-imidazolidin-2-one-hydrojodide Acetonitrile and 2-bromoethanol in the presence of sodium jodide and N-ethyl-diisopropylamine is used.

Melting point: >200° C.

R$_f$ value: 0.55 (silica gel; methylene chloride/methanol/conc. aqueous ammonia=90:10:2)

(6) 1-[trans-4-[2-(methoxycarbonyl)ethyl]cyclohexyl]-3-(methoxycarbonylmethyl)-2,3,4,5-tetrahydro-1H-3-benzazepin-7-yl)-imidazolidin-2-one Acetonitrile and 2-bromoacetate in the presence of sodium jodide and N-ethyl-diisopropylamine are used.

Melting point: 127°–129° C.

R$_f$ value: 0.28 (Reversed phase silica gel; methanol/5% aqueous saline solution=6:4)

EXAMPLE 21

3-[trans-4-[2-(Methoxycarbonyl)ethyl)cyclohexyl]-1-(2,3,4,5-tetrahydro-1H-3-benzazepin-7-yl)-hydantoin-hydrochloride Hydrochloric acid gas is passed for 10 minutes over 920 mg of 3-[trans-4-[2-(methoxycarbonyl)ethyl]cyclohexyl]-1-(3-trifluoroacetyl-2,3,4,5-tetrahydro-1H-3-benzazepin-7-yl)-hydantoin in 50 ml methanol and the mixture is then refluxed for 5 hours. It is cooled, the product is suction filtered, washed with methanol and diethylether and dried at 80° C.

Yield: 770 mg (95% of theory),

Melting point: >250° C.

R$_f$ value: 0.23 (Reversed Phase silica gel; methanol/5% aqueous saline solution=6:4)

The following compounds are obtained analogously to Example 21:

(1) 1-[trans-4-[2-(methoxycarbonyl)ethyl]cyclohexyl]-3-(2,3,4,5-tetrahydro-1H-3-benzazepin-7-yl)-hydantoin-hydrochloride Melting point: >250° C.

$R_f$ value: 0.43 (Reversed Phase silica gel; methanol/5% aqueous saline solution=6:4)

Calc.: C 61.39 H 7.17 N 9.34 Cl 7.88 Found: 61.10 7.21 9.29 8.03

(2) 1-[trans-4-[2-(methoxycarbonyl)ethyl]cyclohexyl]-3-(2,3,4,5-tetrahydro-1H-3-benzazepin-7-yl)-3,4,5,6-tetrahydro-1H-pyrimidin-2-one-hydrochloride $R_f$ value: 0.31 (Reversed Phase silica gel; methanol/5% aqueous saline solution=6:4)

EXAMPLE 22

3-[trans-4-[2-(Methoxycarbonyl)ethyl]cyclohexyl]-1-(3-trifluoroacetyl-2,3,4,5-tetrahydro-1H-3-benzazepin-7-yl)-hydantoin 40 mg of potassium tert.butoxide are added to 2.1 g of N-[trans-4-[2-(methoxycarbonyl)ethyl]cyclohexyl]-N'-[(benzyloxycarbonyl)methyl]-N'-(3-trifluoroacetyl-2,3,4,5-tetrahydro-1H-3-benzazepin-7-yl)-urea in 25 ml of boiling toluene and the mixture is refluxed for 30 minutes. The reaction mixture is cooled, stirred with a few drops of glacial acetic acid, evaporated down and purified by chromatography over a silica gel column using cyclohexane/ethyl acetate (8:2 to 7:3) and crystallised from methanol.

Yield: 0.95 g (55% of theory),

Melting point: 132°–134° C.

$R_f$ value: 0.59 (silica gel; cyclohexane/ethyl acetate=1:1)

EXAMPLE 23

1-[trans-4-[2-(Methoxycarbonyl)ethyl]cyclohexyl]-3-(6,7,8,9-tetrahydro-5H-pyrimido[4,5-d]azepin-2-yl)imidazolidin-2-one 1.0 g of 1-[trans-4-[2-(methoxycarbonyl)ethyl]cyclohexyl]-3-(7-benzyl-6,7,8,9-tetrahydro-5H-pyrimido[4,5-d]azepin-2-yl)-3H-imidazol-2-one are hydrogenated in 15 ml of methanol in the presence of 500 mg of palladium on activated charcoal (10% palladium) for 17 hours at ambient temperature under a hydrogen pressure of 50 psi. The catalyst is filtered off and the filtrate is evaporated down. The residue is used directly to prepare the compound of example 9(16).

$R_f$ value: 0.44 (Reversed Phase silica gel; methanol/5% aqueous saline solution=6:4)

The following compound is obtained analogously to Example 23:

(1) 1-[trans-4-[2-(methoxycarbonyl)ethyl]cyclohexyl]-3-(6,7,8,9-tetrahydro-5H-pyrido[2,3-d]azepin-2-yl)imidazolidin-2-one-hydrochloride.

EXAMPLE 24

1-[2-(Ethoxycarbonyl)ethyl]-3-[4-(3-methyl-2,3,4,5-tetrahydro-1H-3-benzazepin-7-yl)phenyl]-imidazolidin-2-one 3.1 g of (3-methyl-2,3,4,5-tetrahydro-1H-3-benzazepin-7-yl)-boric acid, 4.1 g of 1-[2-(ethoxycarbonyl)ethyl]-3-[4-(trifluoromethylsulfonyloxy)phenyl]-imidazolidin-2-one, 3.5 g tetrakis(triphenylphosphine)-palladium and 6.5 ml of triethylamine are stirred in 25 ml of dimethylformamide under nitrogen for 4 hours at 100° C. The reaction mixture is cooled, evaporated in vacuo and the obtained residue dissolved in methylene chloride. The mixture is filtered over siliceous earth, the filtrate evaporated and the obtained residue is purified by chromatography over a silica gel column with methylene chloride/methanol (100:7).

Yield: 2.7 g (63% of theory), $R_f$ value: 0.31 (silica gel; methylene chloride/methanol= 100:7)

EXAMPLE 25

| Dry ampoule containing 2.5 mg of active substance per 1 ml | |
|---|---|
| Composition: | |
| Active substance | 2.5 mg |
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

EXAMPLE 26

| Dry ampoule containing 35 mg of active substance per 2 ml | |
|---|---|
| Composition: | |
| Active substance | 35.0 mg |
| Mannitol | 100.0 mg |
| Water for injections ad | 2.0 ml |

Preparation:

The active substance and mannitol are dissolved in water. After transferring the solution to the ampoule, it is freeze-dried.

At the point of use, the solution is made up with water for injections.

EXAMPLE 27

| Tablet containing 50 mg of active substance | |
|---|---|
| Composition: | |
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 28

| Tablet containing 350 mg of active substance | |
|---|---|
| Composition: | |
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 29

| Capsules containing 50 mg of active substance | |
|---|---|
| Composition: | |
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing.

This powdered mixture is packed into size 3 hard gelatin oblong capsules in a capsule filling machine.

EXAMPLE 30

| Capsules containing 350 mg of active substance | |
|---|---|
| Composition: | |
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This triturate is added to the mixture of (2) and (4), with thorough mixing.

This powdered mixture is packed into size 0 hard gelatin oblong capsules in a capsule filling machine.

What is claimed is:

1. An imidazolidinone of formula

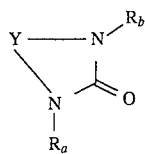

(I)

wherein:

Y is a —$CH_2CH_2$—, —$CH_2CH_2CH_2$—, —CH=CH—, —CH=N—, —N=CH—, —$CH_2$CO— or —CO$CH_2$— group optionally substituted by one or two methyl groups;

$R_a$ is a group of general formula

A—B— wherein

A is a group of the formula

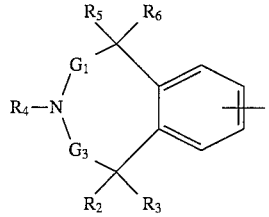

wherein the benzo moiety of the above-mentioned group may be hydrogenated to the corresponding hexahydro-derivative, $G_1$ is a methylene group, $G_3$ is a methylene group, $R_2$ is a hydrogen atom, $R_3$ is a hydrogen atom, $R_4$ is a hydrogen atom, a $C_{1-6}$-alkyl, cyclopropyl, cyclohexyl, cyclopropylmethyl, cyclohexylmethyl, 2-hydroxy-ethyl, allyl, benzyl, carboxymethyl or $C_{1-2}$-alkoxymethyl group, alkoxy carbonylmethyl group $R_5$ is a hydrogen atom, $R_6$ is a hydrogen atom, and B is a bond, a —$CH_2CH_2$— or phenylene group;

$R_b$ is a group of formula

F—E—D— wherein

D is a bond, an alkylene, phenylene or cyclohexylene group;

E is a straight-chained alkylene group which may be substituted by an alkyl or phenyl group, a $C_{2-4}$-alkenylene group, a phenylene group, or E is a straight-chained O-alkylene group linked to the group D via the oxygen atom; and F is a carbonyl group substituted by a hydroxy, alkoxy or $C_{5-6}$-cycloalkoxy group, and the shortest distance between the group F and the ring nitrogen atom of group A is at least 11 bonds;

whilst unless otherwise specified the above-mentioned alkyl, alkylene or alkoxy moieties may each contain 1 to 4 carbon atoms, and each carbon atom in the above mentioned alkylene and cycloalkylene moieties is linked to one heteroatom at most and each of the above-mentioned phenyl or phenylene groups may be substituted by a fluorine, chlorine or bromine atom, by a methyl or methoxy group;

the tautomers, stereoisomers or salts thereof.

2. The imidazolidinone as recited in claim 1, wherein:

Y is a —$CH_2CH_2$—, —CH=CH—, —CH=N—, —N=CH—, —N=C(CH$_3$)—, —$CH_2$CO— or —CO$CH_2$— group;

$R_a$ is a group of general formula

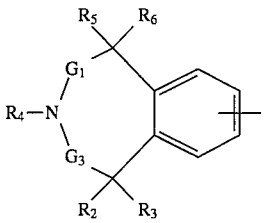

wherein $G_1$ is a methylene group, $G_3$ is a methylene group, $R_2$ is a hydrogen atom, $R_3$ is a hydrogen atom, $R_4$ is a hydrogen atom, a $C_{1-4}$-alkyl, cyclopropylmethyl, 2-hydroxy-ethyl, allyl, benzyl, carboxymethyl or methoxycarbonylmethyl group, $R_5$ is a hydrogen atom, $R_6$ is a hydrogen atom, and $R_b$ is a group of formula

F—E—D— wherein

D is a 1,4-phenylene or 1,4-cyclohexylene group;

E is a —$CH_2CH_2$— group optionally substituted by a methyl or phenyl group, a —CH=CH— group or a —$OCH_2$— group wherein the oxygen atom is linked to group D; and F is a carbonyl group substituted by a hydroxy or $C_{1-4}$-alkoxy group;

the tautomers, stereoisomers or salts thereof.

3. The imidazolidinone as recited in claim 1, wherein:

Y is a —$CH_2CH_2$—, —CH=CH—, —$CH_2CO$— or —$COCH_2$— group;

$R_a$ is a group of general formula

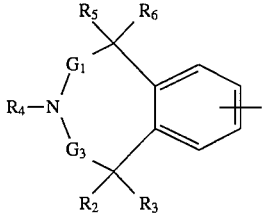

wherein $G_1$ is a methylene group, $G_3$ is a methylene group, $R_2$ is a hydrogen atom, $R_3$ is a hydrogen atom, $R_4$ is a hydrogen atom, a $C_{1-4}$-alkyl, cyclopropylmethyl, 2-hydroxy-ethyl, allyl, benzyl, carboxymethyl or methoxycarbonylmethyl group, $R_5$ is a hydrogen atom, $R_6$ is a hydrogen atom, and $R_b$ is a group of formula

F—E—D— wherein

D is a 1,4-phenylene or 1,4-cyclohexylene group;

E is a —$CH_2CH_2$— group optionally substituted by a methyl or phenyl group, or a —CH=CH— group; and F is a carbonyl group substituted by a hydroxy or $C_{1-4}$-alkoxy group;

the tautomers, stereoisomers or salts thereof.

4. The imidazolidinone as recited in claim 1 selected from the group consisting of:

(a) 1-[4-(2-carboxyethyl)phenyl]-3-(2,3,4,5-tetrahydro-1H-3-benzazepine-7-yl-imidazolidin-2-one, (b) 1-[4-(2-carboxyethyl)phenyl]-3-(3-methyl-2,3,4,5-tetrahydro-1H-3-benzazepin-7-yl)-imidazolidin-2-one, (c) 1-[trans-4-(2-carboxyethyl)cyclohexyl]-3-(2,3,4,5-tetrahydro-1H-3-benzazepin-7-yl)-imidazolidin-2-one, (d) 1-[trans-4-(2-carboxyethyl)cyclohexyl]-3-(3-methyl-2,3,4,5-tetrahydro-1H-3-benzazepin-7-yl)-imidazolidin-2-one, and (e) 1-[trans-4-(2-carboxyethyl)cyclohexyl]-3-(3-ethyl-2,3,4,5-tetrahydro-1H-3-benzazepin-7-yl)-imidazolidin-2-one, or $C_{1-3}$-alkyl esters or salts thereof.

5. 1-[trans-4-(2-carboxyethyl)cyclohexyl]-3-(3-methyl-2,3,4,5-tetrahydro-1H-3-benzazepin-7-yl)-imidazolidin-2-one, $C_{1-3}$-alkyl esters or salts thereof.

6. 1-[trans-4-(2-carboxyethyl)cyclohexyl]-3-(3-methyl-2,3,4,5-tetrahydro-1H-3-benzazepin-7-yl)-imidazolidin-2-one, or salts thereof.

* * * * *